(12) United States Patent
Muñoz Risueño et al.

(10) Patent No.: US 12,109,221 B2
(45) Date of Patent: *Oct. 8, 2024

(54) COMBINATION THERAPY FOR TREATING CANCER

(71) Applicants: LEUKOS BIOTECH, S.L., Barcelona (ES); FUNDACIÓ INSTITUT DE RECERCA CONTRA LA LEUCÈMIA JOSEP CARRERAS, Badalona (ES)

(72) Inventors: Ruth Muñoz Risueño, Barcelona (ES); Mari Carmen Lara Castillo, Barcelona (ES); Amaia Etxabe Alberdi, Barcelona (ES)

(73) Assignees: LEUKOS BIOTECH, S.L., Barcelona (ES); FUNDACIÓ INSTITUT DE RECERCA CONTRA LA LEUCÈMIA JOSEP CARRERAS, Badalona (ES)

( * ) Notice: Subject to any disclaimer, the term of this patent is extended or adjusted under 35 U.S.C. 154(b) by 0 days.

This patent is subject to a terminal disclaimer.

(21) Appl. No.: 17/818,841

(22) Filed: Aug. 10, 2022

(65) Prior Publication Data

US 2023/0122940 A1 Apr. 20, 2023

Related U.S. Application Data

(63) Continuation of application No. 16/478,121, filed as application No. PCT/EP2018/050876 on Jan. 15, 2018, now Pat. No. 11,446,321.

(30) Foreign Application Priority Data

Jan. 16, 2017 (EP) ..................................... 17382015

(51) Int. Cl.
*A61K 31/7068* (2006.01)
*A61K 31/485* (2006.01)
*A61K 31/55* (2006.01)
*A61K 31/706* (2006.01)
*A61P 35/02* (2006.01)

(52) U.S. Cl.
CPC ........ *A61K 31/7068* (2013.01); *A61K 31/485* (2013.01); *A61K 31/55* (2013.01); *A61K 31/706* (2013.01); *A61P 35/02* (2018.01)

(58) Field of Classification Search
None
See application file for complete search history.

(56) References Cited

U.S. PATENT DOCUMENTS 8,058,243 B2 * 11/2011 Tyers ................. G01N 33/5073
514/18.1
2016/0175331 A1 6/2016 Civin et al.

FOREIGN PATENT DOCUMENTS

WO WO-2009016488 A2 2/2009
WO WO-2015197839 A1 * 12/2015 ........... A61K 31/473
WO WO-2016007647 A1 1/2016

OTHER PUBLICATIONS

Tolcher, Anthony W., and Lawrence D. Mayer. "Improving combination cancer therapy: the CombiPlex® development platform." Future Oncology 14.13 (2018): 1317-1332.*
Akhani, S.P., et al., "Anti-diabetic activity of *Zingiber officinale* in streptozotocin-induced type I diabetic rats," J. Pharm Pharmacol 56(1): 101-105, Royal Pharmaceutical Society, England (2010).
Amabeoku, G., et al., "GABAergic and dopaminergic systems may be involved in seizures induced by pyrimethamine in mice," General Pharmacology: The Vascular System 255(6):1269-1277, Elsevier, Netherlands (1994).
Chia, J.S.M., et al., "Zerumbone alleviates chronic constriction injury-induced allodynia and hyperalgesia through serotonin 5-HT receptors," Biomed Pharmacother 83:1303;1310, Elsevier, Netherlands (2016).
Dizeyi, N., et al., "Expression of serotonin receptors and role of serotonin in human prostate cancer tissue and cell lines," The Prostate 59(3), 328-336, Wiley Online Library, United States (2004).
Doherty, E.A., et al., "Ribozyme structures and mechanisms," Annu Rev Biophys Biomol Struct 30:457-475, Annuals Review, United States (2001).
Hakim, L., et al., "Gelam honey and ginger potentiate the anti-cancer effect of 5-FU against HCT 116 colorectal cancer cells," Asian Pac. J Cancer Prev 15(11): 4651-4657, Asian Pacific Organization for Cancer Prevention, Iran (2014).
Kohler, G., et al., "Continuous cultures of fused cells secreting antibody of predefined specificity," Nature 256(5517):495-497, Nature Publishing Group, England (1975).

(Continued)

*Primary Examiner* — Patrick T Lewis
(74) *Attorney, Agent, or Firm* — STERNE, KESSLER, GOLDSTEIN & FOX P.L.L.C.

(57) ABSTRACT

The invention relates to a combination comprising an antineoplastic agent, e.g. an antimetabolite antineoplastic agent and a type 1 serotonin receptor (HTR1) modulator, e.g. a HTR1 antagonist. In addition the invention relates to a pharmaceutical composition comprising a combination of the invention and a pharmaceutically acceptable excipient. The invention also relates to the combination and pharmaceutical composition according to the invention for use in medicine, particularly for use in the prevention and/or treatment of a hematological malignancy.

15 Claims, 18 Drawing Sheets

(56) References Cited

OTHER PUBLICATIONS

Li, X., et al., "Synergistic apoptotic effect of crocin and cisplatin on osteosarcoma cells via caspase induced apoptosis," Toxicol Lett 221(3):197-204, Elsevier, Netherlands (2013).

Millan, M.J., et al., "Differential actions of antiparkinson agents at multiple classes of monoaminergic receptor. I. A multivariate analysis of the binding profiles of 14 drugs at 21 native and cloned human receptor subtypes," J. Pharmacol Exp Ther 303(2):791-804, American Society for Pharmacology and Experimental Therapeutics, United States (2002).

Nichols, D.E., et al., "Serotonin receptors," Chem Rev. 108(5):1614-1641, American Chemistry Society, United States (2008).

Pu, F., et al., "The synergistic anticancer effect of cisplatin combined with *Oldenlandia diffusa* in osteosarcoma MG-63 cell line in vitro," Onco Targets Ther. 9:255-263, Dovepress, United States (2016).

Sharma, C., et al., "Use of gemcitabine and ginger extract infusion may improve the efficiency of cervical cancer treatment," African Journal of Biotechnology 8(24): 7087-7093, Academic Journals, Nigeria (2009).

Suni, M.A., et al., "Flow cytometric analysis of cell signaling proteins," Signal transduction Immunohistochemistry 717:155-169, Methods Mol Biol, United States (2011).

Uzawa, K., et al., "Suppression of metastasis by mirtazapine via restoration of the Lin-7C/$\beta$-catenin pathway in human cancer cells," Sci Rep 4:5433: 1-8, Nature Research, England (2014).

Williams., C., et al., "CAMP detection methods in HTS: selecting the best from the rest," Nat Rev Drug Discov 3(2): 125-135, Nature Publishing Group, England (2004).

Wu, G-S., et al., "Synergistic anti-cancer activity of the combination of dihydroartemisinin and doxorubicin in breast cancer cells," Pharmacol Rep 65(2):453-459, Institute of Pharmacology Polish Academy of Sciences, Poland (2013).

\* cited by examiner

COMBINATION THERAPY FOR TREATING CANCER

CROSS-REFERENCE TO RELATED APPLICATIONS

This application is a continuation of U.S. application Ser. No. 16/478,121, with 371(c) date of Jul. 15, 2019, which issued as U.S. Pat. No. 11,446,321, on Sep. 20, 2022, which is the U.S. national phase application of International Application No. PCT/EP2018/050876, filed Jan. 15, 2018, which claims the priority of European Appl. No. 17382015.0, filed on Jan. 16, 2017, all of which are hereby incorporated by reference in their entireties.

TECHNICAL FIELD OF THE INVENTION

The invention is related to the field of cancer treatment and to augmentation of anti-neoplastic drug efficacy.

BACKGROUND OF THE INVENTION

There are many antineoplastic agents available for treatment of neoplastic diseases. The design or selection of a chemotherapeutic drug for antineoplastic treatment must take into account many factors, depending on the tumor type, the physical condition of the patient and the progression of tumor growth in the patient. Another factor to consider in identifying an effective antineoplastic agent is the degree of selectivity of the agent's cytotoxic effect for the tumor cell over normal host cells.

Toxicity is a major concern for anticancer drugs. These compounds present a narrow therapeutic index, with a small difference between the doses. Approaches to the reduction of chemotherapy-induced toxicity include dose reduction, use of alternate drugs or their analogues, growth factors, and cytoprotective agents.

In addition to the pharmacokinetic changes that occur with age, pharmacodynamic changes such as altered intracellular metabolism of drug and decreased ability to repair DNA occur. With age, the toxicity of normal tissues is altered, and the risk and severity of myelodepression, mucositis, central and peripheral neurotoxicity, and cardiotoxicity also appear to increase.

Newly approved anticancer drugs are associated with increased toxicity, except for agents with a specific molecular target on cancer cells. Management of toxicity leads to a small increase in overall cost of treatment and such toxicity can limit the net benefit of the treatments. Indeed, patients with a poor Eastern Cooperative Oncology Group (ECOG) performance status (ECOG>o=3) do not receive intensive chemotherapy treatment as these patients do not tolerate chemotherapy based on the severe side effects of this treatment. For instance, treatment with chemotherapy such as azacitidine, cytarabine or decitabine gives severe side effects like infections, blood and lymphatic disorders, nervous system disorders, respiratory disorders, gastrointestinal disorders and pyrexia among others. Unwanted side effects may lead to the discontinuation of the optimal treatment regimen and the initiation of a less aggressive and less effective low-dose chemotherapeutic treatment, which is based on palliative care.

In an attempt to reduce the toxic effect of the antineoplastic agents, some synergistic combinations allowing the administration of lower doses of the antineoplastic agent have been developed. The combination of doxorubicin, which produces cardiotoxicity, and dihydroartemisin (Wu G S. et al., Pharmacol Rep. 2013; 65(2):453-9; US20160175331A1) shows synergistic effect so the same anticancer effect is obtained with low doses of the anticancer agent. In addition, cisplatin combined with *Oldenlandia diffusa* induces synergistic anticancer effect in osteosarcoma MG-63 cell line in vitro (Pu Feife. et al., Onco Targets Ther. 2016 Jan. 11; 9:255-63) and the combination of cisplatin with crocin reduces the amount of cisplatin needed as well as its toxic side effect (Li X. et al., Toxicol Lett. 2013 Aug. 29; 221(3):197-204).

WO2009016488 discloses serotonin receptor 2A (HTR2A) antagonists in combination with a secondary treatment for the treatment of cancer, for example breast tumors, gliomas, hormone-refractory prostate cancer and urologic tumors, particularly bladder tumors. This document provides a long list of possible secondary treatments (see paragraphs [0013]-[0014], [0042]-[0049]) as well as a long list of suitable HTR2A antagonists (see paragraphs [0039]) and possible combinations. In the experimental work of WO2009016488, only one combination is tested, mianserin and tamoxifene, in mice xenografted with breast tumor cells. Mianserin is an HTR2A antagonist which is a tetracyclic antidepressant. WO2016007647 discloses nanoparticulated glutaminase inhibitors for the treatment of pancreatic cancer and other glutamine addicted cancers. BPTES (bis-2[5-(phenylacetamido)-1,3,4-thiadiazol-2-yl]ethyl sulfide) is a compound used as antiproliferative but have problems of solubility and metabolic stability. To be effective as glutaminase inhibitor, a compound has to be able to cross cell membranes and reach mitochondria where glutaminase enzyme resides. Thus, in the experimental work of this document, the aim is to identify novel glutaminase inhibitor structures, by maintaining BPES lipophilic structure to ensure compatibility with nanoparticle formulation. The experimental work provides a long list of newly synthesized BPTES analogs as glutaminase inhibitors as well as optimization of nanoparticule formulations including these BPTES. Further, Example 5 page 40 describes the combination of BPTES nanoparticles with non-encapsulated gemcitabine. Apomorphine is simply mentioned in this document as a possible glutaminase inhibitor, but no data supports this statement. The skilled in the art by reading this document can conclude that delivery of glutaminase inhibitors, including apomorphine, have to be enhanced by means of encapsulation in nanoparticles in order to reach the enzyme within the cell structure. Further, the skilled in the art cannot conclude that nanoencapsulated apomorphine can work as serotonin receptor (HTR) antagonist, i.e. doing its effect in the cell membranes where the serotonin receptor is located. Alternatively expressed, by reading this document the skilled person has in practice no motivation to use apomorphine without encapsulation and acting as HTR antagonist. With respect to the use of a nanoencapsulated glutamine inhibitors in combination with chemotherapeutics, the document does not disclose any data supporting the effect of a combination, not even in pancreatic cancer—i.e. the combination related statements may be seen as mere statements that are not supported by any significant verifiable experimental data.

Chhavi Sharma et al. describes that gemcitabine and ginger extract infusion may improve the efficiency of cervical cancer treatment (Chhavi et al. African Journal of Biotechnology, 2009 pp. 7087-7093). Luqman Hakin et al. discloses that ginger potentiates the anti cancer effect of 5-FU (Luqman Hakin et al. Asian Pacific Journal of Cancer Prevention, vol. 15 no. 11, 15 2014 pp. 4651-4657). Gingerols and shogaols (derived from ginger) are described as HTR3 antagonists. HTR3 is the only serotonin receptor that is not a GPCR, but an ion channel. It is structurally and functionally distinct from HTR1 and HTR2. Ginger is administered to help in reducing vomiting and nausea produced by chemotherapeutics.

Thus there is a need in the field of cancer chemotherapy to identify compositions by which the toxic side effects can be reduced without compromising the anticancer efficacy.

SUMMARY OF THE INVENTION

The present disclosure provides in a first aspect, therapeutic combinations comprising at least one antineoplastic agent, e.g. an antimetabolite antineoplastic agent, and at least one type 1 serotonin receptor (HTR1) modulator, e.g. at least one HTR1 antagonist. The term "combination of the invention" as used throughout the specification refers to these combinations.

In a second aspect, the present disclosure also provides pharmaceutical compositions comprising a combination of the invention and at least one pharmaceutically acceptable excipient. The term "pharmaceutical composition of the invention" as used throughout the specification refers to these pharmaceutical compositions.

In a third aspect also provided are combinations of the invention or pharmaceutical compositions of the invention for use in medicine.

In a fourth aspect also provided are combinations of the invention or pharmaceutical compositions of the invention for use in the prevention and/or treatment of cancer.

In a fifth aspect, also provided are combinations of the invention or pharmaceutical compositions of the invention for use in the prevention and/or treatment of a hematological malignancy, e.g., lymphomas, leukemias and myelomas and particularly, acute myeloid leukaemia, myelodysplastic syndrome and myeloproliferative neoplasm.

The present disclosure also provides methods to treat, prevent, or ameliorate the symptoms of hematological malignancies, e.g., lymphomas, leukemias and myelomas and particularly, acute myeloid leukaemia, myelodysplastic syndrome and myeloproliferative neoplasm.

Also provided as articles of manufacture and kits comprising the combinations or pharmaceutical compositions of the invention disclosed herein.

BRIEF DESCRIPTION OF THE DRAWINGS

FIG. 1A. Cell viability was measured by flow cytometry (correct FSC-SSC profile, 7-AAD-, Hoechst33342$^{low}$). Normalized number of live cells is graphed. Bars represent the mean value and error bars represent SEM. * p<0.001; ** p<0.0001. NLC: Number of live cells (referred to control). FIG. 1B. Combination index (CI) value of each combination.

FIG. 2A. Cell viability was measured by flow cytometry (correct FSC-SSC profile, 7-AAD-, Hoechst33342$^{low}$). Normalized number of live cells is graphed. Bars represent the mean value and error bars represent SEM. * p<0.001; ** p<0.0001. NLC: Number of live cells (referred to control). FIG. 2B. Combination index (CI) value of each combination.

FIG. 3A. Cell viability was measured by flow cytometry (correct FSC-SSC profile, 7-AAD-, Hoechst33342$^{low}$). Normalized number of live cells is graphed. Bars represent the mean value and error bars represent SEM. * p<0.001; ** p<0.0001. FIG. 3B. Combination index (CI) value of each combination.

FIG. 6A. Mean Fluorescence Intensity (MFI) of HTR1A and HTR1B. White bars, parental AML cell lines; black bars, Ara-C-resistant AML cell lines. Bars represent the mean value; error bars represent SEM. FIG. 6B. Representative HTR1A and HTR1B expression histogram plot of parental (grey) and Ara-C-resistant cells (black line). FIG. 6C. Correlation between HTR1A and HTR1B expression (MFI) and EC50 for cytarabine. * p<0.5; ** p<0.01. MFIc: Mean Fluorescence Intensity referred to control. MFI: Mean Fluorescence Intensity. HL-60: HL-60 cell line. HL-60 CYT-R: Cytarabine-resistant HL-60 cell line. KG-1: KG-1 cell line. KG-1 CYT-R: Cytarabine-resistant KG-1 cell line. CYT: logarithm Cytarabine concentration.

FIG. 8A. Combination index (CI) value of CLD and APO combination. FIG. 8B. CI value of CLD and MET combination.

FIG. 9A. CI value of FLD and APO combination. FIG. 9B. CI value of FLD and MET combination.

DETAILED DESCRIPTION OF THE INVENTION

Figure 1A:
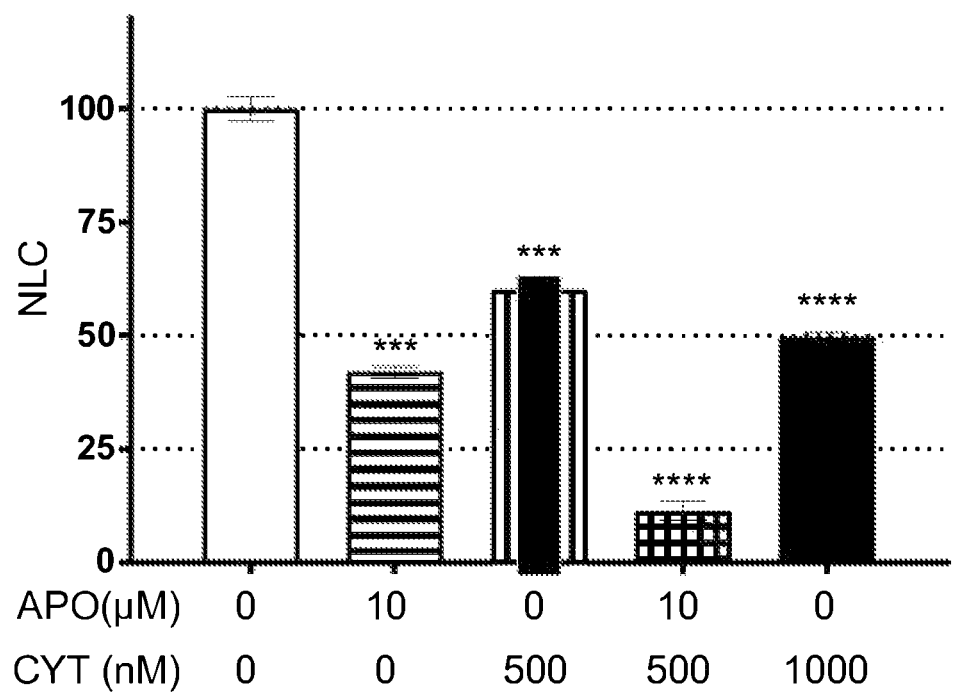
FIGS. 1A and 1B. Cytarabine displayed a synergistic anti-neoplastic effect combined with HTR1 antagonists on AML cells. MonoMac-1 cells were cultured for 72 h in a complete RPMI medium in the presence of 2, 5, 10 μM apomorphine (APO) or methiothepin (MET), and 250, 500, 1000 nM cytarabine (CYT).

The present specification discloses a synergistic anti-cancer effect of several antineoplastic agents, e.g. antimetabolite antineoplastic agents in combination with type 1 serotonin receptor (HTR1) modulators, e.g. HTR1 antagonists, when used in vitro (Examples 1-3) and in vivo (Example 4). Said synergistic effect allows reducing the dose of the antimetabolite antineoplastic agent administered, thus reducing the toxic effect produced in the patient. Unwanted side effects due to antineoplastic agents may lead to the discontinuation of the optimal treatment regimen and the initiation of a less aggressive and less effective low-dose antineoplastic treatment. The use of a HTR1 antagonist in combination with an antineoplastic agent such as cytarabine, decitabine or azacitidine therefore allows for a therapeutically effective dose of antineoplastic agents to be administered at lower levels, thereby avoiding the undesirable sides effects usually associated with higher doses of antineoplastic agents.

It has been determined that the combination of an HTR1 antagonist and an antimetabolite antineoplastic agent is unexpectedly effective for killing cancer cells. As shown herein, serotonin receptor antagonists such as apomorphine, methiothepin or SB-224289 are cytotoxic to cancer cells and particularly in acute myeloid leukemia (AML). Serotonin receptor antagonists at concentrations toxic to cancer cells have also been found to have a relatively limited effect on normal stem cells such as hematopoietic stem cells and normal hematopoietic mature blood cells. Furthermore, as shown in Examples 1-4 and 8-10, the combination of the HTR1 antagonist apomorphine, methiothepine and SB-224289 and the antineoplastic agents cytarabine, decitabine, azacitidine, cladribine, fludarabine and methotrexate resulted in a synergistic effect and a significant reduction in the number of AML cancer cells. The synergistic effect between HTR1 antagonists and antimetabolite antineoplastic agents is also shown in an in vivo xenotransplantation assay where human AML-bearing mice are treated with apomorphine and/or cytarabine (Example 4 FIG. 4). Furthermore, resistance to chemotherapeutic (cytarabine) did not influence the sensitivity to HTR antagonists, Thus, the synergistic effect observed might be due to the mechanism of action of HTR1 antagonists that induce cytarabine sensitivity (Example 5, FIG. 5). Indeed, chemotherapeutic (cytarabine) resistance is accompanied by an overexpression of HTR1 on the surface, suggesting that HTR1 expression may provide survival advantages (Example 6, FIGS. 6A, 6B, and 6C). In addition, the inventors have observed that HTR1 antagonists induce a decreased expression of SPI1 gene, a gene well-known for being related with drug resistance whose downregulation produce antineoplastic agent sensitivity. Thus, HTR1 antagonists make cells more sensitive to antineoplastics (Example 7, FIG. 7).

I. Compositions Comprising an Antimetabolite Antineoplastic Agent and a Type 1 Serotonin Receptor (HTR1) Antagonist In some aspects, the present disclosure provides combinations comprising at least one antineoplastic agent, e.g., an antimetabolite antineoplastic agent and at least one HTR1 modulator, e.g., an HTR1 antagonist. According to the invention the expression "combination" stands for the various combinations of compounds (A) and (B), for example in a composition, in a combined mixture composed from separate formulations of the single active compounds, such as a "tank-mix", and in a combined use of the single active ingredients when applied in a sequential manner, i.e. one after the other with a reasonably short period, such as a few hours or days or in simultaneous administration. In the present invention, compound (A) refers to a therapeutically effective amount of at least one antineoplastic agent, e.g. an antimetabolite antineoplastic agent, or a pharmaceutically acceptable salt thereof and compound (B) refers to at least one HTR1 modulator e.g. a HTR1 antagonist or a pharmaceutically acceptable salt thereof. Preferably the order of applying the compounds (A) and (B) is not essential for working the present invention.

A combination of at least one antineoplastic agent, e.g. an antimetabolite antineoplastic agent and at least one HTR1 modulator, e.g., an HTR1 antagonist can be formulated for its simultaneous, separate or sequential administration. Particularly, if the administration is not simultaneous, the compounds are administered in a close time proximity to each other. Furthermore, compounds are administered in the same or different dosage form or by the same or different administration route, e.g., one compound can be administered topically and the other compound can be administered orally. Suitably, both compounds are administered orally.

The combination of the two compounds, i.e. an antineoplastic agent, e.g., an antimetabolite antineoplastic agent and the HTR1 modulator, e.g., an HTR1 antagonist can be administered:
  as a combination that is being part of the same medicament formulation, the two compounds being then administered always simultaneously.
  as a combination of two units, each with one of the substances giving rise to the possibility of simultaneous, sequential or separate administration.

In a particular embodiment, the antineoplastic agent, e.g. the antimetabolite antineoplastic agent is independently administered from the HTR1 modulator, e.g., the HTR1 antagonist (i.e., in two units) but at the same time.

In another particular embodiment, the HTR1 modulator, e.g. the HTR1 antagonist is administered first, and then the antineoplastic agent e.g. the antimetabolite antineoplastic agent is separately or sequentially administered.

In yet another particular embodiment, the antineoplastic agent, e.g. the antimetabolite antineoplastic agent is administered first, and then the HTR1 modulator, e.g. the HTR1 antagonist is administered, separately or sequentially, as defined.

"Antimetabolite antineoplastic agent", as used herein, relates to a compound that interferes with the cancer cell's metabolism. Some of them replace essential metabolites without performing their functions, while others compete with essential components by mimicking their functions and thereby inhibiting the manufacture of protein in the cell. Antimetabolites are cell cycle phase specific (S phase). Antimetabolite antineoplastic agents and subgroups thereof are well-defined in the ATC/DDD Index (established by the World Health 10 Organization), last update 19 Dec. 2016.

In a particular embodiment, the antimetabolite antineoplastic agent is selected from the group consisting of a folic acid analogue and a nucleoside analogue. In a particular embodiment, the antimetabolite antineoplastic agent is a folic acid analogue. "Folic acid analogue", as used herein, is intended to encompass any analogue of folic acid that contains at least one carboxyl group and that acts as an antimetabolite by interfering with normal folic acid dependent metabolic processes, thus producing the symptoms of a folic acid deficiency.

In a more particular embodiment, the folic acid analogue is selected from the group consisting of methotrexate, raltitrexed, pemetrexed and pralatrexate. In a more particular embodiment, the folic acid analogue is methotrexate.

"Methotrexate", as used herein, relates to the compound (2S)-2-[(4{[(2,4-Diaminopteridin-6-yl)methyl](methyl)amino}benzoyl)amino]pentanedioic acid having the CAS number 59-05-2.

In another particular embodiment, the antimetabolite antineoplastic agent is a nucleoside analogue.

"Nucleoside analogue", as used herein, relates to a compound that resembles naturally occurring nucleosides and acts by causing termination of the nascent DNA chain.

In a particular embodiment, the nucleoside analogue is a purine analogue.

"Purine analogue", as used herein, relates to a compound that mimics the structure of metabolic purines. In a particular embodiment, the purine analogue is selected from the group consisting of mercaptopurine, tioguanine, cladribine, fludarabine, clofarabine and nelarabine. In a more particular embodiment, the purine analogue is mercaptopurine. In another particular embodiment the purine analogue is cladribine. In another particular embodiment, the purine analogue is fludarabine.

"Mercaptopurine", as used herein, relates to the compound 3,7 dihydropurine-6-thione having the CAS number 50-44-2.

"Cladribine", as used herein, relates to the compound 5-(6-Amino-2chloro-purin-9-yl)-2-(hydroxymethyl)oxolan-3-ol having the CAS number 429163-8.

"Fludarabine", as used herein, relates to the compound [(2R,3R,4S,5R)-5-(6-amino-2-fluoro-purin-9-yl)-3,4-dihydroxy-oxolan-2-yl]methoxyphosphonic acid having the CAS number 75607-67-9.

In another particular embodiment, the nucleoside analogue is a "pyrimidine analogue".

"Pyrimidine analogue", as used herein, relates to a compound which mimics the structure of metabolic pyrimidines. Pyrimidine analogues are well-defined in the ATC/DDD Index or Classification System Anatomical, Therapeutic, Chemical Code (established by the World Health Organization and adopted in Europe) group. A pyrimidine analogue can be a thymidine analogue or a cytidine analogue. "Thymidine analogue", as used herein, relates to a compound which mimics the structure of thymidine, a nucleoside molecule formed when thymine is attached to deoxyribose via a β-N3-glycosidic bond. "Cytidine analogue", as used herein, relates to a compound which mimics the structure of cytidine, a nucleoside molecule formed when cytosine is attached to a ribose ring via a β-N1-glycosidic bond.

In a particular embodiment, the pyrimidine analogue is selected from the group consisting of cytarabine, fluorouracil, tegafur, carmofur, gemcitabine, capecitabine, azacitidine, decitabine and trifluridine.

In a particular embodiment, the pyrimidine analogue is cytarabine. In another particular embodiment, the pyrimidine analogue is azacitidine. In another particular embodiment, the pyrimidine analogue is decitabine.

"Cytarabine" or cytosine arabinoside or ara-C(Cytosar-U or Depocyt) refers to the compound 4-amino-1-[(2R,3S,4R,5R)-3,4-dihydroxy-5 (hydroxymethyl)oxolan-2-yl]pyrimidin-2-one having the CAS-number 147-94-4.

"Azacitidine" refers to the compound 4-Amino-1-β-D-ribofuranosyl-1,3,5triazin-2(1H)-one having the CAS number 320-67-2.

"Decitabine" or 5-aza-2'-deoxycytidine refers to the compound 4-Amino-1-(2-deoxy-β-D-erythro-pentofuranosyl)-1,3,5-triazin-2(1H)-one having the CAS number 2353-33-5.

The combination of the invention, in addition to the antimetabolite antineoplastic agent, comprises a HTR1 antagonist.

The combination of the invention can comprise more than one antimetabolite antineoplastic agent and more than one HTR1 antagonist.

"Serotonin receptors", also known as HTR, 5-hydroxytryptamine receptors, 5-HT receptors or 5-HTR, as used herein, are a group of G protein-coupled receptors (GPCRs) and ligand-gated ion channels (LGICs) mostly found in the central and peripheral nervous systems.

"Serotonin receptor (HTR) antagonist" refers to a compound that binds to the 5-HT receptor and lacks any substantial ability to activate the receptor itself. An antagonist can thereby prevent or reduce the functional activation or occupation of the receptor by an agonist or the natural ligand when the agonist is present. The term "antagonist of the 5-HT receptor", as used herein, is intended to encompass both neutral antagonists and inverse agonists. A "neutral antagonist" is a compound that blocks the action of the agonist but has no effect on intrinsic or spontaneous receptor activity. An "inverse agonist" is able to both block the action of the agonist at the receptor and attenuates the constitutive activity of the receptor. The term "antagonist" also includes competitive antagonists, which are drugs that bind to the same site as the natural ligand; noncompetitive antagonists which bind to a different site on the receptor than the natural ligand; reversible antagonists which bind and unbind the receptor at rates determined by receptor-ligand kinetics; and irreversible antagonists which bind permanently to the receptor either by forming a covalent bond to the active site or just by binding so tightly that the rate of dissociation is effectively zero.

The term "HTR1" or "type 1 HTR" or "type 1 5-HT receptor" or "type 1 5HTR" or "5-HT1 receptor" or "5-HTR1", as used herein, relates to a subfamily of 5-HT receptors that bind the endogenous neurotransmitter serotonin (5-hydroxytryptamine, 5-HT). The 5-HT1 receptor subfamily consists of five G protein-coupled receptors (GPCRs) that are coupled to Gi/Go and the term includes HTR1A, HTR1B, HTR1D, HTR1E, and HTR1F. These receptors mediate inhibitory neurotransmission by decreasing cellular levels of cAMP. The complete protein sequence for human type 1A 5-HT receptor has the UniProt accession number P08908 (Nov. 30, 2016). The complete protein sequence for human type 1B 5-HT receptor has the UniProt accession number P28222 (Nov. 30, 2016). The complete protein sequence for human type 1D 5-HT receptor has the UniProt accession number P28221 (Nov. 2, 2016). The complete protein sequence for human type 1E 5-HT receptor has the UniProt accession number P28566 (Nov. 2, 2016). The complete protein sequence for human type 1F 5-HT receptor has the UniProt accession number P30939 (Nov. 2, 2016).

In a particular embodiment, the HTR1 antagonist is type 1A HTR antagonist. In another particular embodiment, the HTR1 antagonist is type 1B HTR antagonist.

The person skilled in the art knows how to determine the affinity of a particular molecule for a type 1 HTR and also to determine if this particular molecule is an antagonist of said receptor. Particular suitable assays are radioligand binding assays to determine the binding affinity, and functional studies of the mobilization of second messengers. For example, the HTR affinity of a molecule can be determined using the methodology described by Millan et al. (Millan et al. J Pharmacol Exp Ther. 2002; 303(2):791-804) (radioligand binding assay) An assay to assess if a compound is a type 1 HTR antagonist is the determination of the Gi activation status and measuring the CAMP production and activation of adenylyl cyclase (Nichols D. E. and Nichols C. E. Chem Rev, 2008; 108(5): 1614-41). The activity of type 1 HTR can be determined by detecting decreasing levels of CAMP (Williams C. Nat Rev Drug Discovery, 2004; 3(2): 125-35) and increasing levels of phosphor-Akt (Suni M A. and Maino V C. Methods Mol Biol 2011; 717:155-69).

Through the examples, different compounds are provided for complying with this ability to antagonize HTR1. Further to said compounds, by means of the methods described before, it is plausible to identify other compounds with the same ability to antagonize HTR1. It is also demonstrated by means of the Examples, that this ability of antagonizing HTR1 in combination with the administration of an antineoplastic agent, e.g. an antimetabolite antineoplastic agent is therapeutically beneficial according to the purposes of the invention. Thus, although some specific compounds have been tested and identified with this beneficial effect, there is no reason to limit the scope of the invention to such compounds because all the steps of the method to get other good candidates are plausibly described herein.

In a more particular embodiment, the type 1A HTR antagonist is selected from the group consisting of GR 125,743; GR 218,231; MPDT; NAN 190; pizotifen; p-MPPI; Rec 15/3079; repinotan; robalzotan; SDZ-216525; tertatolol; UH301; WAY-100135; apomorphine; cyamemazine; flurocarazolol; metergoline; methiothepin; methysergide; SB 224289 and tiospirone. In a more particular embodiment, the type 1A HTR antagonist is a 1A HTR subtype-specific antagonist, more particularly is a 1A HTR subtype-specific antagonist selected from the group consisting of GR 125,743; GR 218,231; MPDT; NAN 190; pizotifen; p-MPPI; Rec 15/3079; repinotan; robalzotan; SDZ-216525; tertatolol; UH301 and WAY-100135.

In another particular embodiment the type 1B HTR antagonist is selected from the group consisting of GR-55562; ocaperidone; SB 272183; SB 649915; SB 714786; SB 236057; apomorphine; cyamemazine; fluro-carazolol; metergoline; methiothepin; methysergide; SB 224289 and tiospirone. In a more particular embodiment, the type 1B HTR antagonist is a 1B HTR subtype-specific antagonist, more particularly is a 1B HTR subtype-specific antagonist selected from the group consisting of GR-55562; ocaperidone; SB 272183; SB 649915; SB 714786 and SB 236057.

In a particular embodiment, the combination of the invention comprises at least one type 1 HTR antagonist. In a more particular embodiment, the combination of the invention comprises apomorphine. In another particular embodiment, the combination of the invention comprises methiothepin. In another embodiment, the combination of the invention comprises amperozide. In another embodiment, the combination of the invention comprises mianserin.

"Apomorphine", as used herein, refers to the compound (6aR)-6-methyl-5,6,6a, 7-tetrahydro-4H-dibenzo[de, g]quinoline-10,11-diol, CAS number 314-19-2.

"Methiothepin" or metitepine, refers to the compound 1-methyl-4-(8methylsulfanyl-5,6-dihydrobenzo[b][1]benzothiepin-6-yl)piperazine, CAS number 74611-28-2.

In a particular embodiment, the combination comprises a pyrimidine analogue and a type 1A HTR antagonist. In another embodiment, the combination of the invention comprises a pyrimidine analogue and a type 1A HTR antagonist. In another embodiment, the combination of the invention comprises a pyrimidine analogue and a type 1B HTR antagonist.

In an embodiment, the combination of the invention comprises a pyrimidine analogue and apomorphine. In an embodiment, the combination of the invention comprises a pyrimidine analogue and methiothepin.

In particular embodiments, the combination of the invention comprises cytarabine and apomorphine; cytarabine and methiothepin; azacitidine and apomorphine; azacitidine and methiothepin; decitabine and apomorphine; or decitabine and methiothepin.

In another particular embodiment, the combination of the invention comprises a folic acid analogue and a type 1A HTR antagonist. In another particular embodiment, the combination of the invention comprises a folic acid analogue and a type 1B HTR antagonist. In another particular embodiment, the combination of the invention comprises a folic acid analogue and apomorphine.

In another particular embodiment, the combination of the invention comprises a folic acid analogue and methiothepin.

In another particular embodiment, the combination of the invention comprises a purine analogue and a type 1A HTR antagonist. In another particular embodiment, the combination of the invention comprises a purine analogue and a type 1B HTR antagonist. In another particular embodiment, the combination of the invention comprises a purine analogue and apomorphine. In another particular embodiment, the combination of the invention comprises a purine analogue and methiothepin.

In another particular embodiment, the combination of the invention comprises methotrexate and apomorphine, methotrexate and methiothepin, mercaptopurine and apomorphine, mercaptopurine and methiothepin, cladribine and apomorphine, cladribine and methiothepin, fludarabine and apomorphine or fludarabine and methiothepin.

In the present invention, when referred to a particular compound is also intended to encompass the pharmaceutically acceptable salt of said compound.

The term "pharmaceutically acceptable salt thereof", as used herein, refers to derivatives of the compounds of the invention wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, e.g., from non-toxic inorganic or organic acids. For example, such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, and toluenesulfonic.

The pharmaceutically acceptable salts of the compounds of the invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are useful. Lists of suitable salts are found in Remington's Pharmaceutical Sciences, 18th ed., Mack Publishing Company, Easton, Pa., 1990, p. 1445.

II. Compositions Comprising at Least an Antineoplastic Agent and at Least a HTR1 Modulator.

In some aspects the present disclosure provides compositions comprising at least an antineoplastic agent, e.g., an antimetabolite antineoplastic agent, and at least one HTR1 modulator, e.g., an HTR1 antagonist (such as a small molecule antagonist, an antibody or antigen binding portion thereof capable of specifically binding to HTR1, a polypeptide antagonist, a nucleic acid such as an siRNA, or any HTR1 antagonists known in the art).

II.i. HTR1 Modulators

As said before, combinations are provided comprising at least one antineoplastic agent, e.g. an antimetabolite antineoplastic agent, and at least one HTR1 modulator, e.g. at least one HTR1 antagonist. The term "modulator", as used herein, refers to a compound modulating the activity of the HTR1 (e.g. by binding to the HTR1 and lacking any substantial ability to activate the receptor itself; or by preventing or reducing the expression of HTR mRNA or HTR protein). The term modulator includes, without limitation, selective inhibitors for HTR1 or for a type of HTR1, non-selective inhibitors that are also capable of acting as inhibitors on other HTR types or on other receptors (e.g. dopamine receptor), antagonists of HTR1, antibodies against HTR1, compounds which prevent expression of HTR1 and compounds which lead to reduced mRNA or protein levels of HTR1. In a preferred embodiment the modulator is an antagonist. The HTR1 modulator can be, among others, a protein, a peptide, interference RNA, an antisense oligonucleotide or a small organic molecule. In a particular embodiment, the HTR1 modulator is HTR1A modulator. In another particular embodiment, the HTR1 modulator is HTR1B modulator.

In other particular embodiments, the HTR1 antagonist is a compound that is also antagonist of dopamine receptor, selected from the group consisting of: Mesoridazine, Sertindole, Butaclamol, Raclopride, Pimozide, S33084 and SB277011-A.

In an embodiment, the HTR1 modulator is an inhibitory antibody. The term "inhibitory antibody" is understood to mean, according to the present invention, an antibody that is capable of binding to HTR1 provoking the inhibition of the activation of said receptor by its natural ligand. Antibodies can be prepared using any method known by a person skilled in the art. Thus, polyclonal antibodies are prepared by immunization of an animal with the protein aimed to be inhibited. Monoclonal antibodies can be prepared using the method described by Kohler, Milstein et al (Nature, 1975, 256: 495). Those antibodies capable of inhibiting HTR1 activity using the abovementioned assays for determination of HTR1 activity will be selected. Suitable antibodies in the present invention include intact antibodies which comprise an antigen-binding variable region and a constant region, fragments "Fab", "F(ab')2", "Fab'", Fv, scFv, diabodies and bispecific antibodies.

In another embodiment, the modulator is an interference RNA. As used herein, the term "interference RNA" or "iRNA" refers to RNA molecules capable of silencing the expression of HTR1 gene or of any gene needed for HTR1 function. To that end, iRNA are typically double-stranded oligonucleotides having at least 30 base pairs in length, and they more preferably comprise about 25, 24, 23, 22, 21, 20, 19, 18 or 17 ribonucleic acid base pairs. Several different types of molecules have been used effectively in iRNA technology including small interfering RNA (siRNA) sometimes known as short interference RNA or silencer RNA, micro RNA (miRNA) which normally differ from siRNA because they are processed from single-stranded RNA precursors and they are shown to be only partially complementary to the target mRNA and short hairpin RNA (shRNA).

Small interfering RNA (siRNA) agents are capable of inhibiting target gene expression by interfering RNA. siRNAs can be chemically synthesized, or can be obtained by in vitro transcription, o can be synthesized in vivo in target cell. Typically, siRNAs consist of a double-stranded RNA from 15 to 40 nucleotides in length and can contain a protuberant region 3' and/or 5' from 1 to 6 nucleotides in length. Length of protuberant region is independent from total length of siRNA molecule. siRNAs act by post-transcriptional degradation or silencing of target messenger.

siRNA can be denominated shRNA (short hairpin RNA) characterized in that the antiparallel strands that form siRNA are connected by a loop or hairpin region. siRNAs are constituted by a short antisense sequence (19 to 25 nucleotides) followed by a loop of 5-9 nucleotides, and the sense strand. shRNAs can be encoded by plasmids or virus, particularly retrovirus and, more particularly, retrovirus and under the control of promoters such as U6 promoter for RNA polymerase III.

The siRNAs of the invention are substantially homologous to type 1 HTR mRNA or its protein-coding genome sequence. The term "substantially homologous" is understood to mean that siRNAs have a sequence sufficiently complementary or similar to target mRNA so that siRNA can be able to provoke mRNA degradation by RNA interference. Suitable siRNAs to provoke interference include siRNAs formed by RNA, as well as siRNAs containing chemically different modifications such as:

siRNAs in which the links between nucleotides are different from those appearing in nature, such as phosphorothioate links.

Stranded-RNA conjugates with a functional reagent, such as a fluorophore.

Modification of the ends of RNA strands, particularly the 3' end by the combination with different functional hydroxyl groups at 2'-position.

Sugar-modified nucleotides such as O-alkylated radicals at 2'-position such as 2'-O-methylribose or 2'-O-fluororibose.

Base-modified nucleotides such as halogenated bases (e.g., 5-bromouracil and 5-iodouracil) or alkylated bases (e.g., 7-methyl-guanosine).

The siRNAs and shRNAs of the invention can be obtained using a series of techniques known to a person skilled in the art. For example, siRNA can be chemically synthesized from protected ribonucleoside phosphoramidites in a conventional DNA/RNA synthesizer. Alternatively, siRNA can be produced by recombinant dicer from plasmid and viral vectors, where the coding region of siRNA strand or strands is under operative control of RNA polymerase III promoters. RNase Dicer processes shRNA into siRNA in cells.

The region which is taken as a basis for the design of siRNA is not limitative and can contain a region of coding sequence (between the initiation codon and the termination codon) or, alternatively, can contain sequences from the 5' or 3' untranslated region, preferably from 25 to 50 nucleotides in length and in any position in 3' position with regard to the initiation codon. A procedure for siRNA design involves the identification of sequence motive AA(N19)TT wherein N can be any nucleotide in the sequence of interest and the selection of those that exhibit a high content in G/C. If said sequence motive is not found, it is possible to identify sequence motive NA(N21) wherein N can be any nucleotide.

In another embodiment, the HTR1 modulator is an antisense oligonucleotide specific to HTR, i.e., molecules whose sequence is complementary to mRNA coding for HTR1, i.e., complementary to cDNA coding strand. The antisense oligonucleotide can be complementary to a complete coding region or a region of same including both the coding region and the 5' and 3' untranslated regions. The antisense oligonucleotides can consist of 5, 10, 15, 20, 25, 30, 35, 40, 45, 50 or more nucleotides in length. The antisense oligonucleotides can be obtained by chemical synthesis or by enzymatic binding reactions widely known to a person skilled in the art. For example, an antisense oligonucleotide can further contain modified nucleotides which increase its biological stability or the stability of the bicatenary DNA-RNA complexes formed between the antisense oligonucleotide and the target polynucleotide, such as phosphorothioate derivatives, peptide nucleic acids and acridine-substituted oligonucleotides. Modified oligonucleotides that can be used for the preparation of antisense nucleic acids include 5-fluorouracil, 5-bromouracil, 5-chlorouracil, 5-iodouracil, hypoxanthine, xanthine, 4-acetyl-cytosine, 5-(carboxyhydroxylmethyl) uracil, 5-carboxymethylaminomethyl-2-thiouridine, 5-carboxymethyl-aminomethyl uracil, dihydrouracil, beta-D-galactosylqueosine, inosine, N6-isopentenyladenine, 1-methylguanine, 1-methylinosine, 2,2dimethylguanine, 2-methyladenine, 2-methylguanine, 3-methylcytosine, 5-methylcytosine, N6-adenine, 7-methylguanine, 5-methylaminomethyluracil, 5methoxyaminomethyl-2-thiouracil, beta-D-mannosylqueosine, 5'methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methyl ester, 3-(3-amino-3-N-2-carboxypropyl)uracil, and 2,6-diaminopurine. Alternatively, the antisense nucleic acid can be produced biologically using an expression vector in which the antisense-oriented nucleic acid has been cloned.

Another group of modulators that can be used in the present invention are catalytically active nucleic acids known as ribozymes. Ribozymes comprise a catalytic region and a second region whose sequence is complementary to target nucleic acid and confers substrate specificity on the ribozyme. After the interaction between the ribozyme and its substrate by hybridization and coupling between complementary regions of target nucleic acid and ribozyme, an activation of the catalytic region is produced provoking the inter- or intramolecular rupture of target nucleic acid. Basic considerations for the design of ribozymes are widely known to a person skilled in the art (see, e.g., Doherty and Doudna (Annu. Rev. Biophys. Biomol. Struct. 2001; 30:457-75).

Other compounds capable of modulating HTR1 and/or the expression thereof that can be used in the invention include aptamers and spiegelmers.

Aptamers and spiegelmers are single-stranded or double-stranded D- or L-nucleic acids that specifically bind to the protein resulting in a modification of the biological activity of the protein. Aptamers and spiegelmers are 15 to 80 nucleotides in length and, preferably, 20 to 50 nucleotides in length.

Suitable methods for determining whether a modulator is capable of decreasing mRNA levels include, without limitation, standard assays for determining mRNA expression levels such as qPCR, RT-PCR, RNA protection analysis, Northern blot, RNA dot blot, in situ hybridization, microarray technology, tag based methods such as serial analysis of gene expression (SAGE) including variants such as Long-SAGE and SuperSAGE, microarrays, fluorescence in situ hybridization (FISH), including variants such as Flow-FISH, qFISH and double fusion FISH (D-FISH), and the like.

Suitable methods for determining whether a modulator acts by decreasing the HTR1 protein levels include the quantification by means of conventional methods, e.g., using antibodies with a capacity to specifically bind to the proteins encoded by the gene (or to fragments thereof containing antigenic determinants) and subsequent quantification of the resulting antibody-antigen complexes.

An HTR1 modulator according to the invention may inhibit HTR1 activity by at least 5%, at least 10%, at least 25%, at least 50%, at least 75%, or at least 90%, and all ranges between 5% and 100%. Suitable methods for determining whether a modulator acts by decreasing HTR1 activity have been previously described.

In particular embodiments, the HTR1 modulator is selected from the group consisting of the compounds of formula I disclosed in EP 0687472 A2, inhibitory antibodies of HTR, an interference RNA specific for the type 1 HTR sequences, an antisense oligonucleotide specific for the type 1 HTR sequences, a ribozyme or DNA enzyme specific for the type 1 HTR sequences.

II.ii. Antineoplastic Agents

According to the ATC/DDD Index (update 19 Dec. 2016), antineoplastic agents are codified as L01 therapeutic group. This group comprises preparations used in the treatment of malignant neoplastic diseases. In particular embodiments the antineoplastic agent is a compound selected from the compounds included in the subgroups of antineoplastic agents group L01. Subgroups include L01A Alkylating agents, L01B Antimetabolites, L01C Plant alkaloids and other natural products, L01D Cytotoxic antibiotics and related substances, and L01X Other antineoplastic agents. Alkylating agents are classified in Nitrogen mustard analogues (e.g. cyclophosphamide, chlorambucil, melphalan, chlormethine, ifosfamide, trofosfamide, prednimustine, bendamustine), Alkyl sulfonates (e.g. busulfan, treosulfan, mannosulfan), Ethylene imines (e.g. thiotepa, triaziquone, carboquone), Nitrosoureas, (e.g. carmustine, lomustine, semustine, streptozocin, fotemustine, nimustine, ranimustine) Epoxides (e.g. etoglucid) and Other alkylating agents (e.g. mitobronitol, pipobroman, temozolomide, dacarbazine). Plant alkaloids and other natural products include Vinca alkaloids and analogues (vinblastine, vincristine, vindesine, vinorelbine, vinflunine, vintafolide), Podophyllotoxin derivatives (e.g. etoposide, teniposide), Taxanes (e.g. paclitaxel, docetaxel, paclitaxel poliglumex, cabazitaxel), and Other plant alkaloids and natural products (e.g. trabectedin). Cytotoxic antibiotics and related substances include Actinomycines (e.g. dactinomycin), Anthracyclines (e.g. doxorubicin, daunorubicin, epirubicin, aclarubicin, zorubicin, idarubicin, mitoxantrone, pirarubicin, valrubicin, amrubicin, pixantrone and related substances), and Other cytotoxic antibiotics (e.g. bleomycin, plicamycin, mitomycin, ixabepilone). Other antineoplastic agents include Platinum compounds (e.g. cisplatin, carboplatin, oxaliplatin, satraplatin, polyplatillen), Methylhydrazines (e.g. procarbazine), Monoclonal antibodies for the treatment of cancer (e.g. edrecolomab, rituximab, trastuzumab, gemtuzumab, cetuximab, bevacizumab, panitumumab, catumaxomab, ofatumumab, ipilimumab, brentuximab, vedotin, pertuzumab, trastuzumab emtansine, obinutuzumab dinutuximab nivolumab pembrolizumab blinatumomab ramucirumab, necitumumab, elotuzumab, daratumumab, mogamulizumab, inotuzumab ozogamicin), Anecortave, indicated for the treatment of exudative age-related macular degeneration, Sensitizers used in photodynamic/radiation therapy (e.g. porfimer sodium, methyl aminolevulinic acid, temoporfin, efaproxiral), Protein kinase inhibitors (e.g. imatinib, gefitinib, erlotinib, sunitinib, sorafenib, dasatinib, lapatinib, nilotinib, temsirolimus, everolimus, pazopanib, vandetanib, afatinib, bosutinib, vemurafenib, crizotinib, axitinib, ruxolitinib, ridaforolimus, regorafenib, masitinib, dabrafenib, ponatinib, trametinib, cabozantinib, ibrutinib, ceritinib, lenvatinib, nintedanib, cediranib, palbociclib, tivozanib, osimertinib, alectinib, rociletinib, cobimetinib, midostaurin, olmutinib), and Other antineoplastic agents (e.g. amsacrine, asparaginase, altretamine, hydroxycarbamide, lonidamine, pentostatin, miltefosine, masoprocol, estramustine, tretinoin, mitoguazone, topotecan, tiazofurine, irinotecan, alitretinoin, mitotane, pegaspargase, bexarotene, arsenic trioxide, denileukin diftitox, bortezomib, celecoxib, anagrelide, oblimersen, sitimagene ceradenovec, vorinostat, romidepsin, omacetaxine mepesuccinate, eribulin, panobinostat, vismodegib, aflibercept, carfilzomib, olaparib, idelalisib, sonidegib, belinostat, ixazomib, talimogene laherparepvec, enetoclax, vosaroxin).

III. Pharmaceutical Compositions

In another aspect, the invention relates to a pharmaceutical composition comprising a combination according to the invention and a pharmaceutically acceptable excipient.

The term "pharmaceutical composition" as used herein refers to a preparation which is in such form as to permit the biological activity of the active ingredients (i.e. the HTR1 modulator, e.g. the HTR1 antagonist and the antineoplastic agent, e.g. an antimetabolite antineoplastic agent) to be effective, and physiologically tolerable, that is, which contains no additional components which are unacceptably toxic to a subject to which the composition would be administered. Such composition can be sterile. Particularly, the term "pharmaceutically acceptable" means it is approved by a regulatory agency of a state or federal government or is included in the U.S. Pharmacopoeia or other generally recognized pharmacopoeia for use in animals, and more particularly in humans.

Appropriate amounts of a compound of the combination of the invention as defined above can be formulated with pharmaceutically acceptable excipients and/or carriers to obtain a pharmaceutical composition for use in medicine, particularly in preventing and/or treating cancer, more particularly in preventing and/or treating a hematological malignancy.

The term "excipient" refers to a vehicle, diluent or adjuvant that is administered with the active ingredient. Such pharmaceutical excipients can be sterile liquids, such as water and oils, including those of petroleum, animal, vegetable or synthetic origin, such as peanut oil, soybean oil, mineral oil, sesame oil and similars. Water or saline aqueous solutions and aqueous dextrose and glycerol solutions, particularly for injectable solutions, are particularly used as vehicles. Suitable pharmaceutical vehicles are described in "Remington's Pharmaceutical Sciences" by E. W. Martin, 21st Edition, 2005; or "Handbook of Pharmaceutical Excipients", Rowe C. R.; Paul J. S.; Marian E. Q., sixth Edition. Suitable pharmaceutically acceptable vehicles include, e.g., water, salt solutions, alcohol, vegetable oils, polyethylene glycols, gelatin, lactose, amylose, magnesium stearate, talc, surfactants, silicic acid, viscous paraffin, perfume oil, monoglycerides and diglycerides of fatty acids, fatty acid esters petroetrals, hydroxymethyl cellulose, polyvinylpyrrolidone and similars.

The pharmaceutical compositions containing the combination of the invention as defined above can occur at any pharmaceutical form of administration (e.g. in the form of, lyophilized powders, slurries, aqueous solutions, lotions, or suspensions) considered appropriate for the selected administration route, including, but not limited to, systemic (e.g. intravenous, subcutaneous, intramuscular injection) intradermal, intraperitoneal, intranasal, epidural, topical, and oral routes, for which it will include the pharmaceutically acceptable excipients necessary for formulation of the desired method of administration. Additionally, it is also possible to administer the composition of the invention as defined above intranasally or sublingually which allows systemic administration by a non-aggressive mode of administration. Also, intraventricular administration can be adequate. A particular route of delivery is oral.

Those skilled in the art are familiar with the principles and procedures discussed.

In a particular embodiment, the composition of the invention is administered intravenously, and more particularly by infusion or bolus injection. Where necessary, the combination of the invention is comprised in a composition also including a solubilizing agent and a local anesthetic to ameliorate any pain at the site of the injection. Generally, the ingredients are supplied either separately or mixed together in unit dosage form, e.g., as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile water for injection or saline can be provided so that the ingredients can be mixed prior to administration.

In cases other than intravenous administration, the composition can contain minor amounts of wetting or emulsifying agents, or pH buffering agents. The composition can be a liquid solution, suspension, emulsion, gel, polymer, or sustained release formulation. The composition can be formulated with traditional binders and carriers, as would be known in the art. Formulations can include standard carriers such as pharmaceutical grades of mannitol, lactose, starch, magnesium stearate, sodium saccharide, cellulose, magnesium carbonate, etc., inert carriers having well established functionality in the manufacture of pharmaceuticals. Various delivery systems are known and can be used to administer a combination or pharmaceutical composition of the present invention including encapsulation in liposomes, microparticles, microcapsules and the like.

Solid dosage forms for oral administration can include conventional capsules, sustained release capsules, conventional tablets, sustained-release tablets, chewable tablets, sublingual tablets, effervescent tablets, pills, suspensions, powders, granules and gels. At these solid dosage forms, the active compounds can be mixed with at least one inert excipient such as sucrose, lactose or starch. Such dosage forms can also comprise, as in normal practice, additional substances other than inert diluents, e.g. lubricating agents such as magnesium stearate. In the case of capsules, tablets, effervescent tablets and pills, the dosage forms can also comprise buffering agents. Tablets and pills can be prepared with enteric coatings.

Liquid dosage forms for oral administration can include emulsions, solutions, suspensions, syrups and elixirs pharmaceutically acceptable containing inert diluents commonly used in the technique, such as water. Those compositions can also comprise adjuvants such as wetting agents, emulsifying and suspending agents, and sweetening agents, flavoring and perfuming agents.

Injectable preparations, e.g., aqueous or oleaginous suspensions, sterile injectable can be formulated according with the technique known using suitable dispersing agents, wetting agents and/or suspending agents. Among the acceptable vehicles and solvents that can be used are water, Ringer's solution and isotonic sodium chloride solution. Sterile oils are also conventionally used as solvents or suspending media.

For topical administration combinations of the invention can be formulated as creams, gels, lotions, liquids, pomades, spray solutions, dispersions, solid bars, emulsions, microemulsions and similars which can be formulated according to conventional methods that use suitable excipients, such as, e.g., emulsifiers, surfactants, thickening agents, coloring agents and combinations of two or more thereof.

Additionally, the combination of the invention can be administered in the form of transdermal patches or iontophoresis devices. In one embodiment, the combination of the invention is administered as a transdermal patch, e.g., in the form of sustained-release transdermal patch. Suitable transdermal patches are known in the art.

Several drug delivery systems are known and can be used to administer the combinations of the invention, including, e.g., encapsulation in liposomes, microbubbles, emulsions, microparticles, microcapsules and similars. The required dosage can be administered as a single unit or in a sustained release form.

Sustainable-release forms and appropriate materials and methods for their preparation are described in, e.g., "Modified-Release Drug Delivery Technology", Rathbone, M. J. Hadgraft, J. and Roberts, M. S. (eds.), Marcel Dekker, Inc., New York (2002), "Handbook of Pharmaceutical Controlled Release Technology", Wise, D. L. (ed.), Marcel Dekker, Inc. New York, (2000). In one embodiment of the invention, the orally administrable form of a combination or pharmaceutical composition of the invention is in a sustained release form further comprises at least one coating or matrix. The coating or sustained release matrix include, without limitation, natural polymers, semisynthetic or synthetic water-insoluble, modified, waxes, fats, fatty alcohols, fatty acids, natural semisynthetic or synthetic plasticizers, or a combination of two or more of them. In one embodiment, a pump can be used (see Langer, supra: Sefton, 1987, CRC Crit. Ref. Biomed. Eng. 14:201). In another embodiment, polymeric materials can be used see, Medical Applications of Controlled Release, Langer and Wise (eds.), 1974, CRC Pres., Boca Raton, Fla. Other controlled release systems are discussed in the review by Langer, 1990, Science 249:1527-1533.

Enteric coatings can be applied using conventional processes known to experts in the art, as described in, e.g., Johnson, J. L., "Pharmaceutical tablet coating", Coatings Technology Handbook (Second Edition), Satas, D. and Tracton, A. A. (eds), Marcel Dekker, Inc. New York, (2001), Carstensen, T., "Coating Tablets in Advanced Pharmaceutical Solids", Swarbrick, J. (ed.), Marcel Dekker, Inc. New York (2001), 455-468.

A pharmaceutical composition of the present disclosure can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present disclosure. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition of the present invention include, but are not limited to the SOLOSTART pen (Sanofi-Aventis), the FLEXPEN™ (Novo Nordisk), and the KWIKPEN™ (Eli Lilly), the SURECLICK™ Autoinjector (Amgen, Thousand Oaks, Calif.), the PENLET™

(Haselmeier, Stuttgart, Germany), the EPIPEN (Dey, L. P.), and the HUMIRA™ Pen (Abbott Labs, Abbott Park III), to name only a few.

IV. Medical Uses

In another aspect, the invention relates to a combination or a pharmaceutical composition according to the invention for use in medicine.

In another aspect, the invention relates to a combination or a pharmaceutical composition according to the invention for use in the prevention and/or treatment of cancer.

Alternatively, the invention relates to the use of a combination or a pharmaceutical composition of the invention for the preparation of a medicament for the prevention and/or treatment of cancer.

Alternatively, the invention relates to a method for preventing and/or treating cancer comprising administering a combination or a pharmaceutical composition of the invention to a subject in need thereof.

In another aspect, the invention relates to a combination or a pharmaceutical composition according to the invention for use in the prevention and/or treatment of a hematological malignancy.

Alternatively, the invention relates to the use of a combination or a pharmaceutical composition of the invention for the preparation of a medicament for the prevention and/or treatment of a hematological malignancy.

Alternatively, the invention relates to a method for preventing and/or treating a hematological malignancy comprising administering a combination or a pharmaceutical composition of the invention to a subject in need thereof.

In another aspect, the invention relates to a combination or a pharmaceutical composition according to the invention for use in the prevention and/or treatment of a solid tumor.

Alternatively, the invention relates to the use of a combination or a pharmaceutical composition of the invention for the preparation of a medicament for the prevention and/or treatment of a solid tumor.

Alternatively, the invention relates to a method for preventing and/or treating a solid tumor comprising administering a combination or a pharmaceutical composition of the invention in a subject in need thereof.

As used herein the terms "treat," "treatment," or "treatment of" refers to reducing the potential for a certain disease or disorder, reducing the occurrence of a certain disease or disorder, and/or a reduction in the severity of a certain disease or disorder, preferably, to an extent that the subject no longer suffers discomfort and/or altered function due to it. For example, "treating" can refer to the ability of a therapy (i.e. the HTR1 modulator, e.g. the HTR1 antagonist and the antineoplastic agent, e.g. an antimetabolite antineoplastic agent) when administered to a subject, to prevent a certain disease or disorder from occurring and/or to cure or to alleviate a certain disease symptoms, signs, or causes. "Treating" also refers to mitigating or decreasing at least one clinical symptom and/or inhibition or delay in the progression of the condition and/or prevention or delay of the onset of a disease or illness. Thus, the terms "treat," "treating" or "treatment of" (or grammatically equivalent terms) refer to both prophylactic and therapeutic treatment regimes. Particularly, "treatment", as used herein, relates to the administration of a combination according to the invention or of a pharmaceutical composition according to the invention to a subject suffering from a hematological malignancy or a solid tumor including the administration in an initial or early stage of a disease, wherein the object is to prevent or slow down (lessen) an undesired physiological change or disorder.

The present disclosure provides methods and compositions generally providing a therapeutic benefit or desired clinical results. A therapeutic benefit is not necessarily a cure for a particular disease or disorder, but rather encompasses a result which most typically includes alleviation of the disease or disorder or increased survival, elimination of the disease or disorder, reduction or alleviation of a symptom associated with the disease or disorder, prevention or alleviation of a secondary disease, disorder or condition resulting from the occurrence of a primary disease or disorder, diminishment of extent of disease, stabilized (i.e., not worsening) state of disease, delay or slowing of disease progression, amelioration or palliation of the disease state, and remission (whether partial or total), whether detectable or undetectable and/or prevention of the disease or disorder. Treatment also means prolonging survival as compared to expected survival if not receiving the treatment.

The term "prevention", "preventing" or "prevent", as used herein, relates to the administration of a combination according to the invention or of a pharmaceutical composition according to the invention to a subject who has not been diagnosed as possibly having a haematological malignancy or a solid tumor at the time of administration, but who would normally be expected to develop said disease or be at increased risk for said disease. The prevention intends to avoid the appearance of said disease. The prevention can be complete (e.g. the total absence of a disease). The prevention can also be partial, such that for example the occurrence of a disease in a subject is less than that which would have occurred without the administration of the combination or composition of the present invention. Prevention also refers to reduced susceptibility to a clinical condition.

The term "subject" or "individual" or "animal" or "patient" includes any subject, particularly a mammalian subject, for whom diagnosis, prognosis, or therapy is desired. Mammalian subjects include humans, domestic animals, farm animals, and zoo or pet animals such as dogs, cats, guinea pigs, rabbits, rats, mice, horses, cattle, cows, and so on. In a particular embodiment of the invention, the subject is a mammal. In a more particular embodiment of the invention, the subject is a human, particularly a human of any race and sex.

In some embodiments, a subject is a naïve subject. A naïve subject is a subject that has not been administered a therapy, e.g. an antineoplastic agent.

In another embodiment, a subject has received therapy and/or one or more doses of a therapeutic agent to treat the haematological malignancy.

The term "haematological malignancy" refers to a type of cancer that affects blood, bone marrow, and lymph nodes, and includes lymphomas, myelomas and leukemias. Historically, scientists and physicians have classified these diseases by their locations in the body, the appearance of affected cells under the microscope, and the natural progression of the diseases. In leukemia, the cancerous cells are discovered circulating in the blood and bone marrow, while in lymphoma, the cells tend to aggregate and form masses, or tumors, in lymphatic tissues. Myeloma is a tumor of the bone marrow, and involves a specific subset of white blood cells that produce a distinctive protein.

Haematological malignancies can derive from either of the two major blood cell lineages: myeloid and lymphoid lineages. The myeloid lineage normally produces granulocytes, erythrocytes, thrombocytes, macrophages and mast cells; the lymphoid cell lineage produces B, T, NK lymphocytes and plasma cells. Non-limitative, illustrative examples of haematological malignancies are Acute lymphoblastic leukaemia (ALL), Acute myelogenous leukaemia (AML), Chronic lymphocytic leukaemia (CLL), Chronic myelogenous leukaemia (CML), Acute monocytic leukaemia (AMOL), Hodgkin's lymphomas, non-Hodgkin's lymphomas and myelomas.

In a particular embodiment, the hematological malignancy is a leukaemia. In a more particular embodiment, the leukaemia is selected from the group consisting of acute myeloid leukaemia (AML), acute lymphoblastic leukaemia (ALL), chronic lymphocytic leukemia (CLL), and chronic myeloid leukaemia (CML).

"Leukaemia", as used herein, refers to a type of cancer of the blood or bone marrow characterized by an abnormal increase of immature white blood cells called "blasts" and that originates in blood-forming tissue. All leukaemias start in the bone marrow where developing blood cells, usually developing white cells, undergo a malignant (cancerous) change. This means that they multiply in an uncontrolled way crowding the marrow and interfering with normal blood cell production. Increasing numbers of abnormal cells, called blast cells or leukaemic blasts eventually spill out of the bone marrow and travel around the body in the blood stream. In some cases these abnormal cells accumulate in various organs including the lymph nodes, spleen, liver and central nervous system (brain and spinal cord). Leukaemia is a broad term covering a spectrum of diseases and they are broadly classified by how quickly the disease develops, and by the type of blood cell involved. In turn, it is part of the even broader group of diseases affecting the blood, bone marrow, and lymphoid system, which are all known as haematological neoplasms. There are four major kinds of leukaemia: Acute lymphoblastic leukaemia, or ALL; Acute myeloid leukaemia, or AML; Chronic lymphocytic leukaemia, or CLL; Chronic myelogenous leukaemia, or CML.

"Acute Myeloid Leukaemia (AML) or acute myelogenous leukaemia or acute nonlymphocytic leukaemia (ANLL)" is a cancer of the myeloid line of blood cells, characterized by the rapid growth of abnormal white blood cells (myeloblasts) that accumulate in the bone marrow and interfere with the production of normal blood cells. The symptoms of AML are caused by replacement of normal bone marrow with leukaemic cells, which causes a drop in red blood cells, platelets and normal white blood cells. The combination of a myeloperoxidase or Sudan black stain and a nonspecific esterase stain on blood and blood marrow smears are helpful in distinguishing AML from ALL.

"Acute lymphoblastic leukaemia (ALL) or acute lymphoid leukaemia" is an acute form of leukaemia, or cancer of the white blood cells, characterized by the overproduction of cancerous, immature white blood cells-known as lymphoblasts.

"Chronic lymphocytic leukaemia (CLL) or B-cell chronic lymphocytic leukaemia (B-CLL)" is a type of cancer that causes the body to produce large numbers of white blood cells (B cell lymphocytes).

"Chronic myelogenous leukaemia (CML)" also known as "chronic myeloid leukaemia" or "chronic granulocytic leukaemia (CGL)" is a type of cancer that causes the body to produce large numbers of white blood cells (myelocytes). In CML a proliferation of mature granulocytes (neutrophils, eosinophils and basophils) and their precursors is found. It is associated with a characteristic 15 chromosomal translocation called the Philadelphia chromosome.

In a particular embodiment, the hematological malignancy is a lymphoma.

"Lymphoma", as used herein relates to a cancer that develops in the lymphatic system from cells called lymphocytes. Lymphomas arise when developing lymphocytes undergo a malignant change and multiply in an uncontrolled way. Increasing numbers of abnormal lymphocytes, called lymphoma cells accumulate and form collections of cancer cells called malignant tumours in lymph nodes and other parts of the body. There are dozens of subtypes of lymphomas, which are broadly divided into two main groups: Hodgkin lymphoma (also known as Hodgkin's disease) and Non-Hodgkin lymphomas (NHL) that can be divided into B-cell and T-cell type. In a particular embodiment, the lymphoma is Hodgkin's lymphoma (HL). In another particular embodiment, the lymphoma is Non-Hodgkin lymphoma (NHL).

In another particular embodiment, the hematological malignancy is a myeloma.

"Myeloma" also known as "multiple myeloma" as used herein, is a cancer of plasma cells. Plasma cells are mature B-lymphocytes that live predominantly in the bone marrow and normally produce antibodies. In myeloma, plasma cells undergo a malignant (cancerous) change and multiply in an uncontrolled way producing large number of abnormal plasma cells, called myeloma cells and causing problems in different parts of the body. There are several subtypes of myeloma. In each case of myeloma, only one type of immunoglobulin is overproduced, but this varies from patient to patient. Types of myeloma are for example Monoclonal Gammopathy of Undetermined Significance (MGUS), Asymptomatic Myeloma, Smoldering Multiple Myeloma (SMM), Symptomatic or Active Myeloma, Light Chain Myeloma, Nonsecretory Myeloma and Plasmacytoma. In a particular embodiment, the myeloma is selected from the group consisting of Monoclonal Gammopathy of Undetermined Significance (MGUS), Asymptomatic Myeloma, Smoldering Multiple Myeloma (SMM), Symptomatic or Active Myeloma, Light Chain Myeloma, Nonsecretory Myeloma and Plasmacytoma.

In a particular embodiment, the hematological malignancy is a myeloid neoplasm.

"Myeloid neoplasm", as used herein, relates to clonal diseases of hematopoietic stem or progenitor cells. The term "myeloid" includes all cells belonging to the granulocyte (i.e., neutrophil, eosinophil, basophil), monocyte/macrophage, erythroid, megakaryocyte, and mast cell lineages. Such neoplasm can be present in the bone marrow and peripheral blood. They result from genetic and epigenetic alterations that perturb key processes such as self-renewal, proliferation and impaired differentiation. Based on the morphology, cytochemistry, immunophenotype, genetics, and clinical features of myeloid disorders, the World Health Organization (WHO) categorizes myeloid neoplasms into five primary types: (1) acute myeloid leukemia; (2) myelodysplastic syndromes (MDS); (3) myeloproliferative neoplasms (MPN); (4) myelodysplastic and myeloproliferative (MDS/MPN) neoplasms; and (5) myeloid neoplasms associated with eosinophilia and abnormalities of growth factor receptors derived from platelets or fibroblasts. In a particular embodiment, the myeloid neoplasm is selected from the group consisting of acute myeloid leukemia (AML), myelodysplastic syndrome (MDS), myeloproliferative neoplasm (MPN), myelodysplastic and myeloproliferative (MDS/MPN) neoplasm, and myeloid neoplasm associated with eosinophilia and abnormalities of growth factor receptors derived from platelets or fibroblasts.

In a particular embodiment, the myeloid neoplasm is acute myeloid leukemia.

In another particular embodiment, the myeloid neoplasm is a myelodysplastic syndrome.

"Myelodysplastic syndrome" (MDS), as used herein, refers to a heterogeneous group of closely related clonal hematopoietic disorders commonly found in the aging population. All are characterized by one or more peripheral blood cytopenias. Bone marrow is usually hypercellular, but rarely, a hypocellular marrow mimicking aplastic anemia can be seen. Bone marrow cells display aberrant morphology and maturation (dysmyelopoiesis), resulting in ineffective blood cell production. There are several different types of MDS and the disease can vary in its severity and the degree to which normal blood cell production is affected. About 30% of people with MDS will progress to a form of cancer called acute myeloid leukaemia (AML). It is sometimes referred to as a pre-leukaemic disorder.

In another particular embodiment, the myeloid neoplasm is a myeloproliferative neoplasm.

"Myeloproliferative neoplasm (MPN)", as used herein relates to clonal hematopoietic stem cell disorders characterized by proliferation of one or more of the myeloid lineages. Each of these disorders involves dysregulation at the multipotent hematopoietic stem cell (CD34) and clonal myeloproliferation and the absence of dyserythropoiesis, dysgranulopoiesis and monocytosis.

In another particular embodiment, the myeloid neoplasm is a myelodysplastic and myeloproliferative neoplasm.

"Myelodysplastic and myeloproliferative neoplasms (MDS/MPN)", as used herein, relates to clonal myeloid disorders that possess both dysplastic and proliferative features but are not properly classified as either myelodysplastic syndromes (MDS) or chronic myeloproliferative disorders (CMPD). The MDS/MPN category includes myeloid neoplasms with clinical, laboratory, and morphologic features that overlap MDS and MPN.

In another particular embodiment, the myeloid neoplasm is a myeloid neoplasm associated with eosinophilia and abnormalities of growth factor receptors derived from platelets or fibroblasts.

"Myeloid neoplasms associated with eosinophilia and abnormalities of growth factor receptors derived from platelets or fibroblasts", as used herein, relates to malignancies that arise by forming abnormal fusion genes that encode altered surface or cytoplasmic proteins that activate signal transduction pathways. There are different subtypes, all of them characterized by eosinophilia, although the clinical presentation of each subtype varies.

In another particular embodiment, the hematological malignancy is a lymphoid neoplasm.

"Lymphoid Neoplasm", as used herein relates to a disease derive from the clonal expansion and proliferation of B- and T-lymphocytes. They encompass a heterogeneous group of lymphomas and leukemias including B-cell, T-cell, and natural killer (NK)-cell disorders.

In another particular embodiment, the hematological malignancy is at precancerous stage. The term "precancerous stage", as used herein, refers to one hyperproliferative disorder or premalignancy condition that can develop into cancer.

"Solid tumor" or solid cancers are neoplasms (new growth of cells) or lesions (damage of anatomic structures or disturbance of physiological functions) formed by an abnormal growth of body tissue cells other than blood, bone marrow or lymphatic cells. A solid tumor consists of an abnormal mass of cells which may stem from different tissue types such as liver, colon, breast, or lung, and which initially grows in the organ of its cellular origin. However, such cancers may spread to other organs through metastatic tumor growth in advanced stages of the disease.

Examples of solid tumors are carcinomas, sarcomas, germinomas and blastomas.

Carcinomas are cancers derived from epithelial cells and account for 80% to 90% of all cancer cases since epithelial tissues are most abundantly found in the body. This group includes many of the most common cancers, particularly in the aged, and include lung cancer, colorectal cancer, pancreatic cancer, larynx cancer, tongue cancer, prostate cancer, breast cancer, ovarian cancer, liver cancer, head and neck cancer, esophageal cancer, renal cancer, endometrial cancer, gall bladder cancer, bladder cancer and gastric cancer. Carcinomas are of two types: adenocarcinoma and squamous cell carcinoma.

Adenocarcinoma develops in an organ or gland and squamous cell carcinoma originates in squamous epithelium. Adenocarcinomas may affect mucus membranes and are first seen as a thickened plaque-like white mucosa. These are rapidly spreading cancers.

Sarcomas are cancers arising from connective tissue including muscles, bones, cartilage and fat. Examples of sarcomas include osteosarcoma (of the bone), chondrosarcoma (of the cartilage), leiomyosarcoma (smooth muscles), rhabdomyosarcoma (skeletal muscles), mesothelial sarcoma or mesothelioma (membranous lining of body cavities), fibrosarcoma (fibrous tissue), angiosarcoma or hemangioendothelioma (blood vessels), liposarcoma (adipose or fatty tissue), glioma or astrocytoma (neurogenic connective tissue found in the brain), myxosarcoma (primitive embryonic connective tissue) and mesenchymous or mixed mesodermal tumor (mixed connective tissue types).

Germinomas refer to germ cell tumors, derived from pluripotent cells, most often presenting in the testicle or the ovary (seminoma and dysgerminoma, respectively).

Blastomas are cancers derived from immature precursor cells or embryonic tissue. Blastomas are more common in children than in older adults. Examples of blastomas include hepatoblastoma, medulloblastoma, nephroblastoma, pancreatoblastoma, pleruropulmonary blastoma, retinoblastoma and glioblastoma multiforme.

Cancers that can be treated or prevented by the medical uses of the present invention are solid tumors, e.g. lung cancer, colorectal cancer, pancreatic cancer, larynx cancer, tongue cancer, breast cancer, ovarian cancer, prostate cancer, liver cancer, head and neck cancer, esophageal cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, dysgerminoma, embryonal carcinoma, Wilms' tumor, cervical cancer, testicular tumor, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma.

Effectiveness of the combination and pharmaceutical composition of the invention can be determined by analyzing the haematological response (measure the numbers of white cells, red cells and platelets and the levels of hemoglobin and hematocrit), cytogenetic response and/or serological tumor markers.

In a particular embodiment, the cancer or hematological malignancy to be treated with the combination of the invention or the pharmaceutical composition of the invention is a cancer or a hematological malignancy characterized by having cells which express HTR1.

In order to determine if the cancer cell or hematological malignant cell expresses HTR1, the expression of said receptor can be determined using any method known in the art, such as those described in WO 2015/197839 based on detecting type 1 HTR mRNA or protein in a sample as a whole, in cells of a sample and/or in the non-cellular fraction of a sample.

The expression "detecting the expression" refers to detecting the presence of a cancer cell or haematological cell in a sample carrying a type 1 HTR on its surface or expressing type 1 HTR mRNA. Said detection can be qualitative or quantitative.

The combinations and pharmaceutical compositions for use in the medical treatments according to the invention should be administered in a pharmaceutical or therapeutically effective amount.

The expression "pharmaceutical or therapeutically effective amount", as used herein, is understood as an amount capable of providing a therapeutic effect, some improvement or benefit to a subject having a hematological malignancy or a solid tumor. Thus, a "pharmaceutical or therapeutically effective" amount is an amount that provides some alleviation, mitigation, and/or decrease in at least one clinical symptom of a hematological malignancy or a solid tumor. Those skilled in the art will appreciate that therapeutic effects need not be complete or curative, as long as some benefit is provided to the subject. The term also encompasses the amount capable of reducing or preventing the hematological malignancy or a solid tumor. The pharmaceutically or therapeutically effective amount can be determined by the person skilled in the art by commonly used means. The amount of the combination of the invention or the pharmaceutical compositions according to the invention will vary depending upon the subject and the particular mode of administration. Those skilled in the art will appreciate that dosages can also be determined with guidance from Goodman and Goldman's The Pharmacological Basis of Therapeutics, Ninth Edition (1996), Appendix II, pp. 1707-1711 and from Goodman and Goldman's The Pharmacological Basis of Therapeutics, Tenth Edition (2001), Appendix II, pp. 475-493.

The appropriate dosage of the active principle or principles within the combination or pharmaceutical composition will depend on the type of cancer to be treated, the severity and course of the disease, whether the composition is administered for preventive or therapeutic purposes, previous therapy, the patient's clinical history and response to the compounds, and the discretion of the attending physician. The amount of the combination of the invention or the pharmaceutical compositions according to the invention is suitably administered to the patient at one time or over a series of treatments. Depending on the type and severity of the disease, an appropriate dosage level will generally be about 0.01 to 500 mg per kg patient body weight per day which can be administered in single or multiple doses. Particularly, the dosage level will be about 0.1 to about 250 mg/kg per day; more particularly about 0.5 to about 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5 or 5 to 50 mg/kg per day. For oral administration, the compositions are particularly provided in the form of tablets containing 1.0 to 1000 milligrams of the active ingredient, particularly at least about 1.0, at least about 5.0, at least about 10.0, at least about 15.0, at least about 20.0, at least about 25.0, at least about 50.0, at least about 75.0, at least about 100.0, at least about 150.0, at least about 200.0, at least about 250.0, at least about 300.0, at least about 400.0, at least about at least about 500.0, at least about 600.0, at least about 750.0, at least about at least about 800.0, at least about 900.0, and at least about 1000.0 milligrams of the active ingredient for the symptomatic adjustment of the dosage to the patient to be treated.

For intravenous administration, the combination or the pharmaceutical compositions according to the invention is particularly administered at a dose of about 0.1 to about 10 mg per patient per day, more particularly from 0.1 to 9 mg per patient per day, more particularly from 0.1 to 8 mg per patient per day, more particularly from 0.1 to 7, more particularly from 0.1 to 6 mg per patient per day, more particularly from 0.1 to 5 mg per patient per day mg per patient per day, more particularly from 0.1 to 4 mg per patient per day, more particularly from 0.1 to 3 mg per patient per day, more particularly from 0.1 to 2 mg per patient per day, more particularly from 0.1 to 1 mg per patient per day. Dosages from 0.1 up to about 100 mg per patient per day may be used, particularly from 0.1 to 90 mg per patient per day, more particularly from 0.1 to 80 mg per patient per day, more particularly from 0.1 to 70 mg per patient per day, more particularly from 0.1 to 60 mg per patient per day, more particularly from 0.1 to 50 mg per patient per day, more particularly from 0.1 to 40 mg per patient per day, more particularly from 0.1 to 30 mg per patient per day, more particularly from 0.1 to 20 mg per patient per day; particularly when the drug is administered to a secluded site and not into the blood stream, such as into a body cavity or into a lumen of an organ. Substantially higher dosages are possible in topical administration.

In a particular embodiment, the combination or the pharmaceutical composition of the invention comprises an antineoplastic agent, e.g. an antimetabolite antineoplastic agent, in an amount between about 1 and 3000 mg/m$^2$. Particularly, when the antimetabolite antineoplastic agent is a folic acid analogue, its amount in the combination or in the pharmaceutical composition is up to 3000 mg/m$^2$; when the antimetabolite antineoplastic agent is a pyrimidine analogue, its amount in the combination or in the pharmaceutical composition is between about 1000 and 3000 mg/m$^2$ (with the exception of decitabine, azacitidine and fluorouracil, which are under these amounts); when the antimetabolite antineoplastic agent is a purine analogue, its amount in the combination or in the pharmaceutical composition is between about 5 and 200 mg/m$^2$.

In a particular embodiment, the combination or the pharmaceutical composition of the invention comprises cytarabine in an amount between about 1 and 3000 mg/m$^2$. In a particular embodiment, the combination or the pharmaceutical composition of the invention comprises decitabine in an amount between about 0.1 and 20 mg/m$^2$. In a particular embodiment, the combination or the pharmaceutical composition of the invention comprises azacitidine in an amount between 0.5 and 75 mg/m$^2$. In a particular embodiment, the combination or the pharmaceutical composition of the invention comprises the HTR1 antagonist in an amount between about 0.1 and 100 mg/m$^2$.

In particular embodiments, the combination or pharmaceutical composition comprises at least one HTR1 antagonist and at least one antimetabolite antineoplastic agent in a ratio comprised between 500:1 and 2:1. In particular embodiments, the combination or pharmaceutical composition comprises at least one HTR1 antagonist and cytarabine in a ratio comprised between 40:1 and 2:1. Examples of amounts of the HTR1 antagonist (HTR1 antag) and cytarabine (cyt) in the combination or the pharmaceutical composition can be 50 mg/m$^2$ HTR1 antag+1.25 mg/m$^2$ cyt; 50 mg/m$^2$ HTR1 antag+25 mg/m$^2$ cyt; 100 mg/m$^2$ HTR1 antag+2.5 mg/m$^2$ cyt; 100 mg/m$^2$ HTR1 antag+50 mg/m$^2$ cyt.

In particular embodiments, the combination or pharmaceutical composition comprises at least one HTR1 antagonist and azacitidine in a ratio comprised between 100:1 and 2:1. Examples of amounts of the HTR1 antagonist (HTR1 antag) and azacitidine (aza) in the combination or the pharmaceutical composition can be 50 mg/m$^2$ HTR1 antag+ 0.5 mg/m$^2$ aza; 50 mg/m$^2$ HTR1 antag+25 mg/m$^2$ aza; 100 mg/m$^2$ HTR1 antag+1 mg/m$^2$ aza; 100 mg/m$^2$ HTR1 antag+ 50 mg/m$^2$ aza.

In particular embodiments, the combination or pharmaceutical composition comprises at least one HTR1 antagonist and decitabine in a ratio comprised between 500:1 and 50:1. Examples of amounts of the HTR1 antagonist (HTR1 antag) and decitabine (deci) in the combination or the pharmaceutical composition can be 50 mg/m$^2$ HTR1 antag+ 0.1 mg/m$^2$ deci; 50 mg/m$^2$ HTR1 antag+1 mg/m$^2$ deci; 100 mg/m$^2$ HTR1 antag+0.2 mg/m$^2$ deci; 100 mg/m$^2$ HTR1 antag+2 mg/m$^2$ deci; 50 mg/m$^2$ HTR1 antag+15 mg/m$^2$ deci; 100 mg/m$^2$ HTR1 antag+15 mg/m$^2$ deci.

In some embodiments, the combination or the pharmaceutical composition according to the invention can be administered at a fixed dose. In other embodiments, it can be administered as a variable dose. In some embodiments, it can be administered as a single dose. In other embodiments, it can be administered in multiple doses, e.g. two or more doses administered daily, weekly, biweekly, or monthly, particularly once or twice per day.

V. Method for Monitoring the Effect of the Therapy

This disclosure also provides methods for detecting the effectiveness of the combinations and pharmaceutical compositions of the invention provided herein through determining the protein expression level or gene expression level of HTR1 as biomarkers. The inventors have found that presence of expression of HTR1 correlates with a good response to treatment with the combinations and the pharmaceutical compositions provided herein.

Thus, in another aspect, the invention relates to an in vitro method for monitoring the effect of the therapy ("therapy" hereinafter referred to the combinations or the pharmaceutical compositions of the invention, i.e. the HTR1 modulator, e.g. the HTR1 antagonist and the antineoplastic agent, e.g. an antimetabolite antineoplastic agent) in a subject suffering from a haematological malignancy or a solid tumor and being treated with said combination or pharmaceutical composition which comprises: a) Determining the expression level of type 1 HTR in cells of a sample from said subject selected from the group consisting of bone marrow, blood and lymph nodes, and b) Comparing said level with the expression level of type 1 HTR in cells of a sample from said subject at an earlier point of time, wherein a decrease of the expression level of type 1 HTR with respect to the level determined in a sample from said subject at an earlier point of time is indicative that the therapy is being effective or wherein an increase of the expression level of type 1 HTR with respect to the level determined in a sample from said subject at an earlier point of time is indicative that the therapy is being ineffective.

The present disclosure also provides a method of treating a patient having a hematological malignancy or a solid tumor comprising administering the therapy if HTR1 expression is detected in a sample taken from the patient, wherein said administration is effective to prevent and/or treat the hematological malignancy or the solid tumor in the subject.

Also provided is a method of treating a patient having a hematological malignancy or a solid tumor comprising (a) submitting a sample taken from the patient for measurement of the level of expression of HTR1, and (b) administering the therapy to the subject if HTR1 expression is detected in the sample, wherein said administration is effective to prevent and/or treat the hematological malignancy or the solid tumor in the subject.

In addition, the present disclosure provides a method of treating a patient having a hematological malignancy or a solid tumor comprising (a) measuring the level of expression of HTR1 in a sample taken from the patient, (b) determining whether the patient's level of expression of HTR1 is above a predetermined HTR1 expression level of a one or more control samples, and (c) advising a healthcare provider to administer the therapy to the subject, wherein said administration is effective to prevent and/or treat the hematological malignancy or the solid tumor in the subject.

Also provided is a method of determining whether to treat a patient diagnosed with a hematological malignancy or a solid tumor comprising (a) measuring, or instructing a clinical laboratory to measure the level of expression of HTR1 in a sample taken from the patient; and (b) treating, or instructing a healthcare provider to treat, the patient by administering the therapy if HTR1 expression is detected in the sample, wherein said administration is effective to prevent and/or treat the hematological malignancy or the solid tumor in the subject.

The disclosure provides also a method of selecting a patient diagnosed with a hematological malignancy or a solid tumor as a candidate for treatment with the therapy comprising (a) measuring, or instructing a clinical laboratory to measure the level of expression of HTR1 in a sample taken from the patient; and (b) treating, or instructing a healthcare provider to treat the patient by administering the therapy if HTR1 expression is detected in the sample, wherein said administration is effective to prevent and/or treat the hematological malignancy or the solid tumor in the subject.

In a preferred embodiment, the haematological malignancy is leukaemia, and more preferably acute myeloid leukaemia.

Methods for determining the expression level of type 1 5-HTR are described in detail in WO2015/197839, methods which are incorporated by reference herein.

In a preferred embodiment, the in vitro method for monitoring the effect of the therapy in a subject suffering from a haematological malignancy or a solid tumor comprises determining the level of type 1 HTR. In a more preferred embodiment, the type 1 HTR is selected from the group consisting of HTR-1A and HTR-1B.

In a preferred embodiment, the method comprises determining the expression level of HTR-1A and HTR-1B.

In another preferred embodiment, the blood sample is peripheral blood.

In another preferred embodiment, the in vitro method for monitoring the effect of the therapy in a subject suffering from a haematological malignancy or a solid tumor comprises determining the expression level of type 1 HTR by measuring the level of mRNA encoded by the type 1 HTR genes, or of variants thereof. In another preferred embodiment, the expression level of type 1 HTR is determined by measuring the level of type 1 HTR proteins, or of variants thereof.

In a more preferred embodiment, the mRNA expression level is determined by PCR. In another preferred embodiment, the expression level of proteins or of variants thereof is determined by Western blot or immunocytochemistry. In a more preferred embodiment, the expression level of type 1 HTR is determined by semi-quantitative PCR.

VI. Articles of Manufacture and Kits

The disclosure also provides articles of manufacture comprising any one of the combinations or the pharmaceutical compositions disclosed herein, in one or more containers. In some embodiments, the article of manufacture comprises, e.g., a brochure, printed instructions, a label, or package insert directing the user (e.g., a distributor or the final user) to combine and/or use the compositions of the article of manufacture for the prevention and/or treatment of a hematological malignancy or a solid tumor.

In some embodiments, the article of manufacture comprises, e.g., bottle(s), vial(s), cartridge(s), box(es), syringe(s), injector(s), or any combination thereof. In some embodiments, the label refers to use or administration of the combinations or the pharmaceutical compositions in the article of manufacture according to the methods disclosed herein. In some aspects, the label suggests, e.g., a regimen for use, a regimen for treating, preventing, or ameliorating a hematological malignancy or a solid tumor.

This disclosure also provides kits for detecting the effectiveness of the combinations and pharmaceutical compositions provided herein (e.g., to determine the protein expression level or gene expression level of HTR)1, e.g., through an immunoassay method or nucleic acid detection method. Such kits can comprise containers, each with one or more of the various reagents (e.g., in concentrated form) utilized in the method, including, e.g., one or more antibodies capable to specifically binding to at least one biomarker (e.g., HTR1), or nucleic acid probes capable of specifically hybridizing to cDNA or mRNA for at least one biomarker. One or more antibodies against at least one biomarker, e.g., capture antibodies, or oligonucleotide probes can be provided already attached to a solid support. One or more antibodies against at least one biomarker, e.g., detection antibodies, or oligonucleotide probes can be provided already conjugated to a detectable label, e.g., biotin or a ruthenium chelate.

The kit can also provide reagents and instrumentation to support the practice of the assays provided herein. In certain aspects, a labeled secondary antibody can be provided that binds to the detection antibody. A kit provided according to this disclosure can further comprise suitable containers, plates, and any other reagents or materials necessary to practice the assays provided herein.

In some embodiments, a kit comprises one or more nucleic acid probes (e.g., oligonucleotides comprising naturally occurring and/or chemically modified nucleotide units) capable of hybridizing a subsequence of a biomarker (HTR1) with high stringency conditions. In some aspects, one or more nucleic acid probes (e.g., oligonucleotides comprising naturally occurring and/or chemically modified nucleotide units) capable of hybridizing a subsequence of a biomarker under high stringency conditions are attached to a microarray chip.

A kit provided according to this disclosure can also comprise brochures or instructions describing the process. Test kits can include instructions for carrying out one or more biomarker detection assays, e.g., immunoassays or nucleic acid detection assays. Instructions included in the kits can be affixed to packaging material or can be included as a package insert. While the instructions are typically written or printed materials they are not limited to such. Any medium capable of storing such instructions and communicating them to an end user is contemplated. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

The contents of all cited references (including literature references, patents, patent applications, and websites) that may be cited throughout this application are hereby expressly incorporated by reference in their entirety for any purpose, as are the references cited therein. All terms as used herein, unless otherwise stated, shall be understood in their ordinary meaning as known in the art. Other more specific definitions for certain terms as used in the present application are as set forth below and are intended to apply uniformly throughout the description and claims unless an otherwise expressly set out definition provides a broader definition. Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. Furthermore, the present invention covers all possible combinations of particular and particular embodiments described herein.

In this specification and the appended claims, the singular forms "a", "an" and "the" include plural referents unless the context clearly dictates otherwise.

The terms "a" (or "an"), as well as the terms "one or more," and "at least one" can be used interchangeably herein. Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone). The term "about" as used in connection with a numerical value throughout the specification and the claims denotes an interval of accuracy, familiar and acceptable to a person skilled in the art. In general, such interval of accuracy is +15%. Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure. Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or aspects of the disclosure, which can be had by reference to the specification as a whole. Accordingly, the terms defined immediately below are more fully defined by reference to the specification in its entirety.

The invention will be described by way of the following examples which are to be considered as merely illustrative and not limitative of the scope of the invention.

EXAMPLES

Synergy is determined herein by means of the Combination Index Model, described previously (Chou T C, Pharmacological Reviews 58: 621-681, 2006). The CI was measured using Compusyn open software. CI values below 1 indicate synergism. CI values about 1 indicate additivism and CI values above 1 indicate antagonisms.

The maximum concentrations corresponding to the EC50 (that dose which produces 50% cell death) and two lower doses corresponding to ½ and ⅕ of the EC50 have been chosen for each compound.

Example 1. Synergistic Effect of Cytarabine and HTR1 Antagonists

In order to study the effects of antineoplastic agents (cytostatic drug) in combination with HTR antagonists type 1, AML cell lines (TPH-1 and MonoMac1) were treated with different concentrations of HTR1 antagonists (apomorphine and methiothepin) in the presence of a range of concentrations of antineoplastics (cytarabine, azacytidine and decitabine). Cytarabine is an antineoplastic agent widely used in the treatment of lymphomas and leukemias.

Figure 1B:
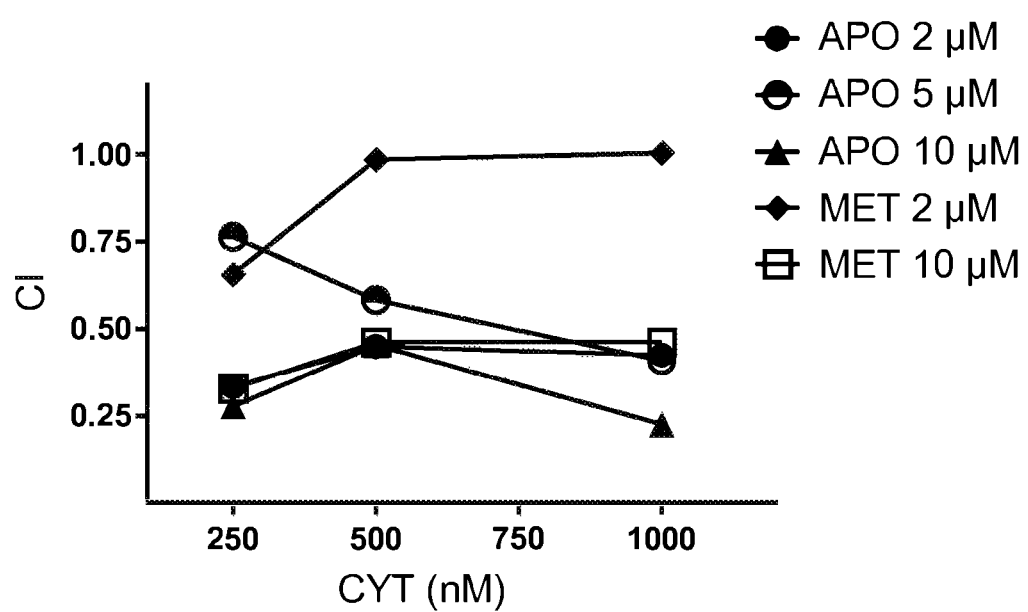

Cell viability was measured by flow cytometry (live cells according to the correct FSC-SSC profile, 7-AAD negativity and Hoechst 33342 positivity) 72 h after treatment (FIG. 1A). As shown in FIG. 1B, both apomorphine and methiothepin act synergically with cytarabine according to the combination index model (Tang et al. Front Pharmacol 2015; 6:181). The synergic effect was detected in a molar range from 40:1 to 2:1 (HTR1 antagonist:cytarabine).

Example 2—Synergistic Effect of Azacitidine and HTR1 Antagonists

Figure 2A:
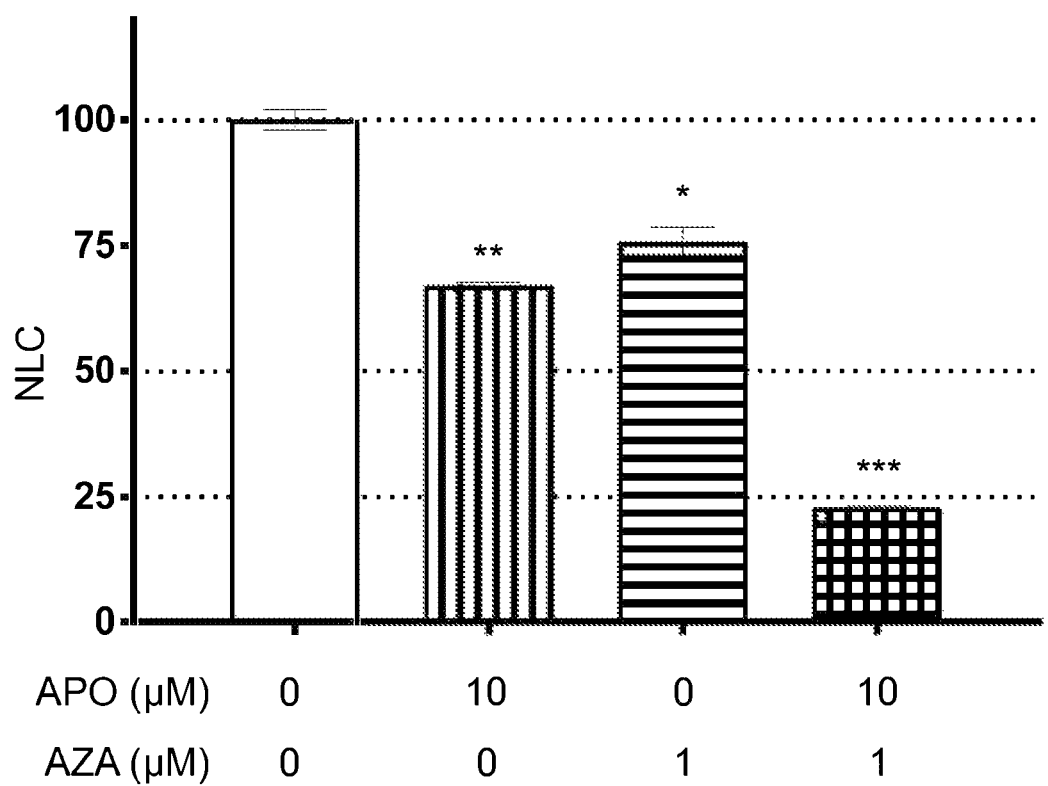
FIGS. 2A and 2B. Azacitidine displayed a synergistic anti-neoplastic effect combined with HTR1 antagonists on AML cells. MonoMac-1 cells were cultured for 72 h in a complete RPMI medium in the presence of 2, 5, 10 μM apomorphine (APO) or methiothepin (MET), and 100, 200, 1000 nM azacitidine (AZA).
Figure 2B:
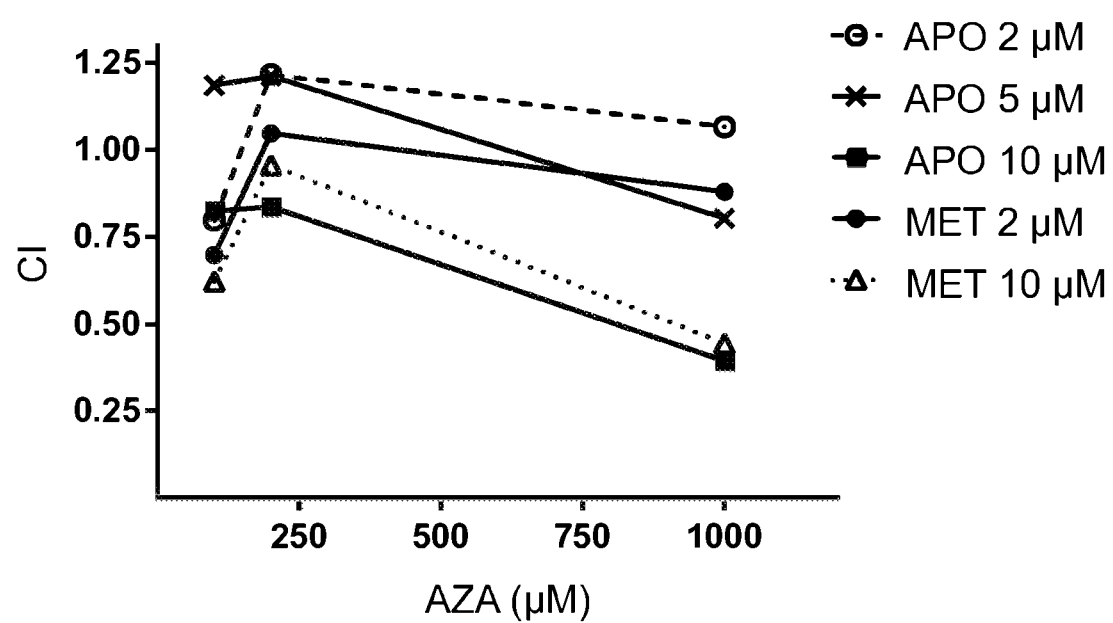

Next, the inventors examined the interaction between HTR1 antagonists and azacitidine. Azacitidine is an antineoplastic drug used for myeloid neoplasias. AML cell lines (HL-60 and MonoMac-1) were treated with different concentrations of HTR1 antagonists (apomorphine and methiothepin) in the presence of a wide range of concentrations of azacitidine. Cell viability was measured by flow cytometry (live cells according to the correct FSC-SSC profile, 7-AAD negativity and Hoechst 33342 positivity) 72 h after treatment. As shown in FIG. 2A and FIG. 2B, both HTR1 antagonists displayed a synergically anti-leukemic effect from a molar relationship of 100:1 to 2:1 (HTR1:azacitidine).

Example 3—Synergistic Effect of Decitabine and HTR1 Antagonists

Figure 3A:
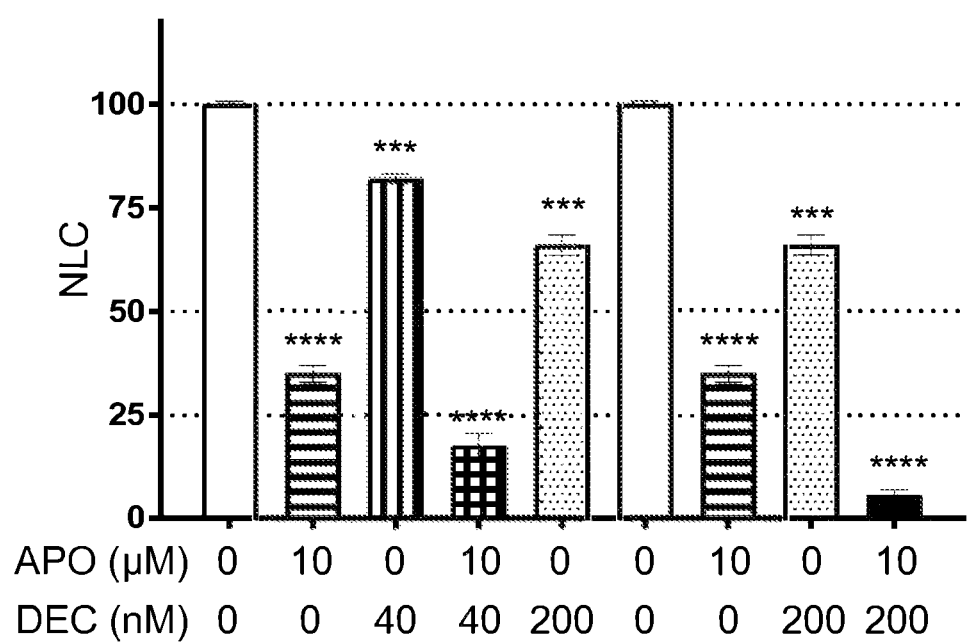
FIGS. 3A and 3B. Decitabine displayed a synergistic anti-neoplastic effect combined with HTR1 antagonists on AML cells. MonoMac-1 cells were cultured for 72 h in a complete RPMI medium in the presence of 2, 5, 10 μM apomorphine (APO) or methiothepin (MET), and 20, 40, 100 nM decitabine (DEC). NLC: Number of live cells (referred to control).
Figure 3B:
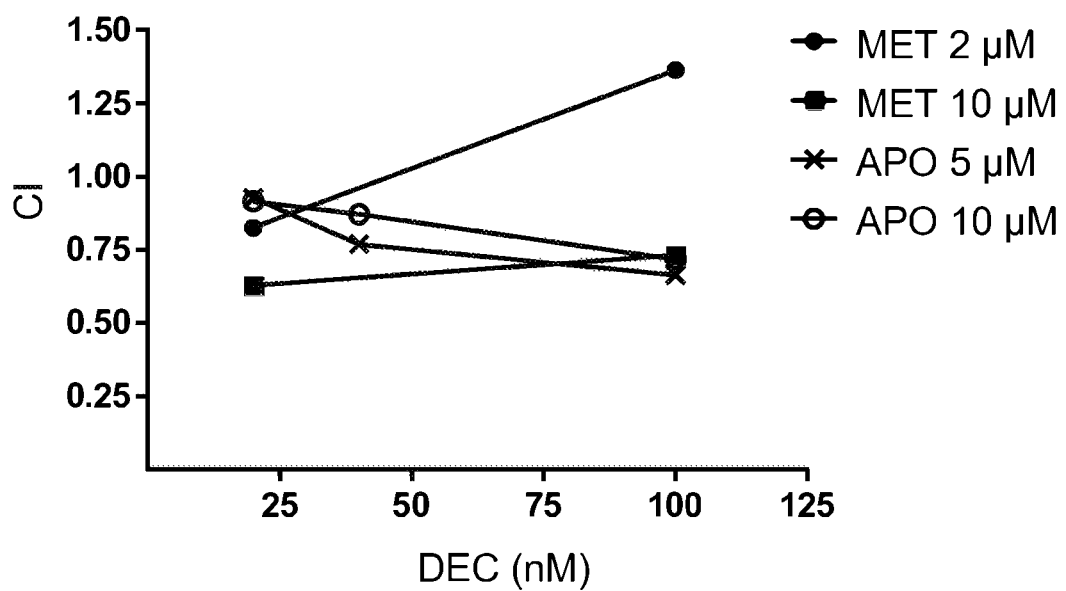

Similarly, decitabine was also interrogated for its potential cytotoxic interaction with HTR1 antagonists. Decitabine is a cytostatic drug indicated for myeloid neoplasias. AML cell lines (HL-60 and MonoMac-1) were treated with different concentrations of HTR1 antagonists (apomorphine and methiothepin) in the presence of a range of concentrations of decitabine. 72 h after treatment, cell viability was measured by flow cytometry (live cells according to the correct FSC-SSC profile, 7-AAD negativity and Hoechst 33342 positivity). As shown in FIGS. 3A and 3B, both HTR1 antagonists displayed a synergically anti-leukemic effect from a molar relationship of 500:1 to 50:1 (HTR1:decitabine).

Example 4—Synergistic Effect In Vivo

Figure 4:
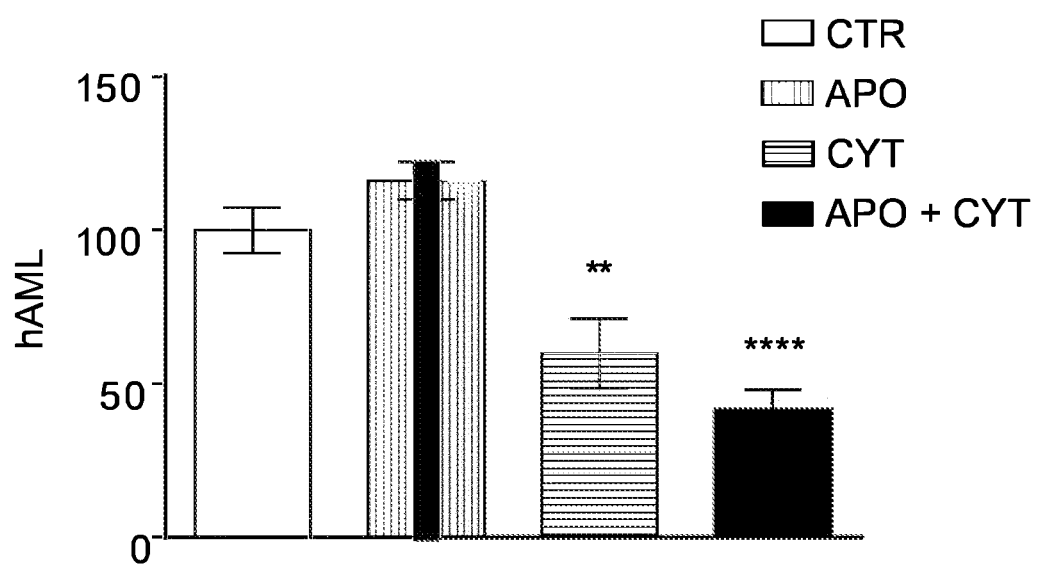
FIG. 4. Apomorphine and cytarabine synergistically acted as anti-AML agents in vivo. Bulsulfan-conditioned NSG adult mice were intravenously injected with $1\times10^6$ MonoMac-1 AML cells. One week after transplantation, mice were treated with 5 mg/kg apomorphine (APO) and/or 30 mg/kg cytarabine (CYT) daily for 5 days. Mice were culled and bones were harvested. Human leukemia cells were detected based on the expression of hCD45 on the surface membrane by flow cytometry. Normalized number of human AML cells against control-treated mice is represented. Bars correspond to mean values and error bars to SEM.  p<0.01; ** p<0.0001. hAML: #human AML cells (referred to 15 control). CTR: Control.

In order to verify that the synergic cytotoxic effect was also detectable in vivo, pharmacological-conditioned NSG mice were transplanted intravenously with $1 \times 10^6$ MonoMac-1 AML cells. One week after transplantation, mice were treated for 5 days with 5 mg/kg apomorphine and/or 30 mg/kg cytarabine, both of them intraperitoneally. Mice were culled and bones were harvested and analyzed for human leukemia by flow cytometry. As shown in FIG. 4, Ara-C and apomorphine also showed a synergistic effect (EOBA>25%) in in vivo treatment of AML-bearing mice.

Example 5-Expression of HTR1A and HTR1B Correlates with Cytarabine Resistance

Figure 5:
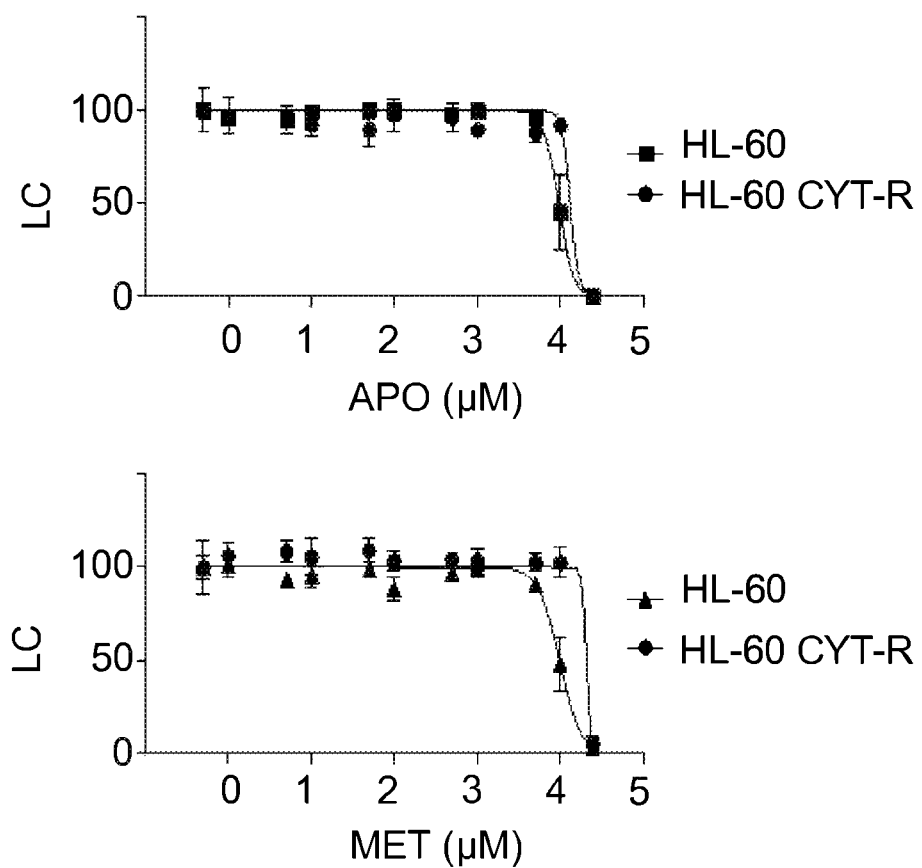
FIG. 5. Resistance to cytarabine did not affect the sensitivity to HTR1 antagonists. Parental and Cytarabine-resistant (CYT-R) HL-60 and KG-1 AML cells were cultured at a $3.5\times10^5$ cells/mL in complete RPMI in 96-well plates. Apomorphine or methiothepin were added at the concentration indicated. At 72 h post-treatment, cells were analyzed by flow cytometry to measure cell viability (correct FSC-SSC profile, 7-AAD-, Hoechst33342$^{low}$). Normalized number of live cells against vehicle-treated control samples is represented. Error bars represent SEM. LC: #live cells (referred to control). APO: logarithm Apomorphine concentration. MET: logarithm Methiothepin concentration. HL-60: HL-60 cell line. HL-60 CYT-R: Cytarabine-resistant HL-60 cell line. KG-1: KG-1 cell line. KG-1 CYT-R: Cytarabine-resistant KG-1 cell line.
Figure 5:
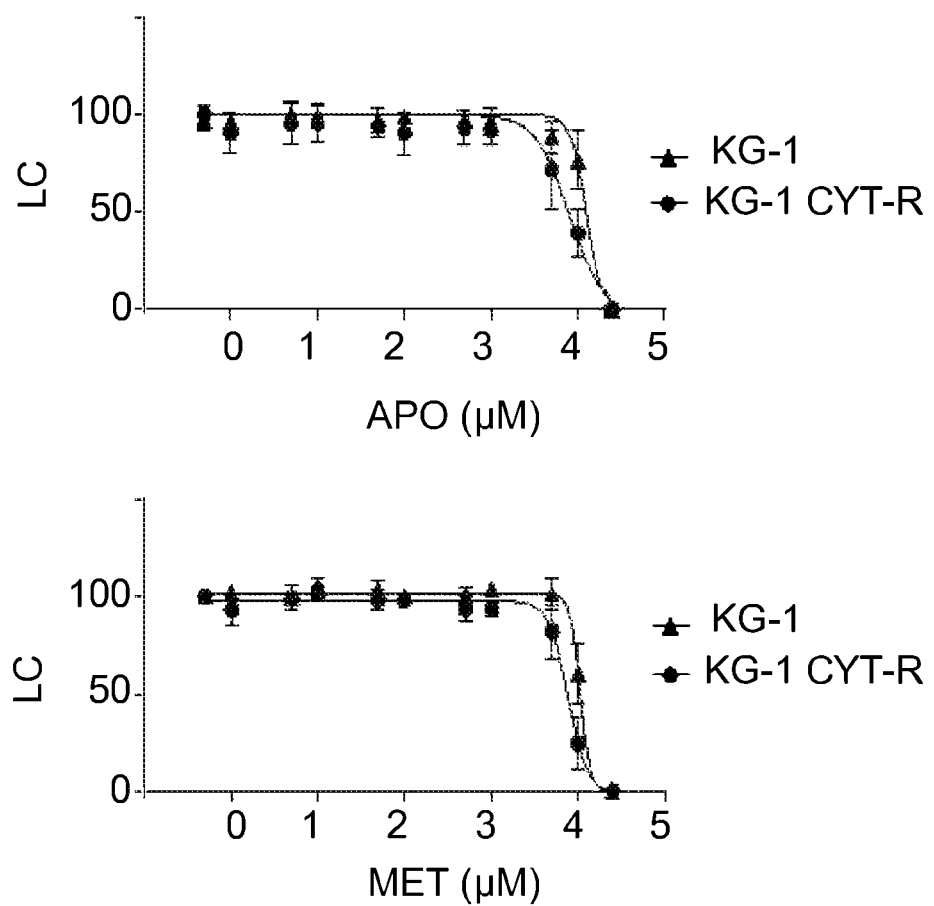

The sensitivity to HTR1 antagonists was studied in Ara-C-resistant-AML cell lines (Cornet-Masana et al. Oncotarget 2016; 7(17):23239-50). Both HL-60 and KG-1 parental cell lines displayed equivalent EC50 values for HTR1 antagonists (apomorphine and methiothepin) to Ara-C-resistant HL-60 and KG15 1 (FIG. 5).

Example 6-HTR1A and HTR1B Expression in Relation to Cytarabine Treatment

Figure 6A:
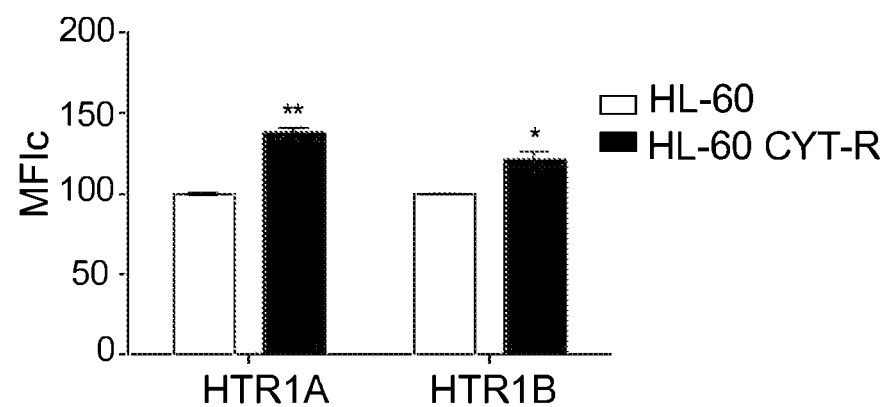
FIGS. 6A, 6B, and 6C. HTR1A and HTR1B expression correlated with sensitivity to cytarabine treatment. Parental and Ara-C-resistant HL-60 and KG-1 cells were stained on cell surface with HTR1A and HTR1B. The expression level was measured by flow cytometry.
Figure 6A:
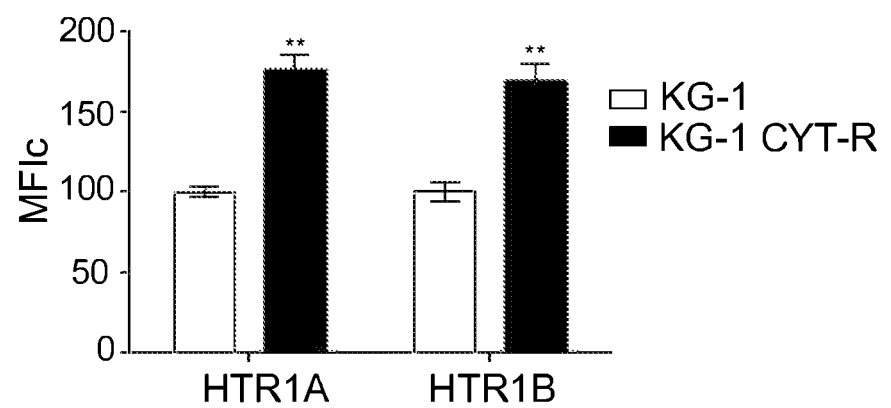
Figure 6B:
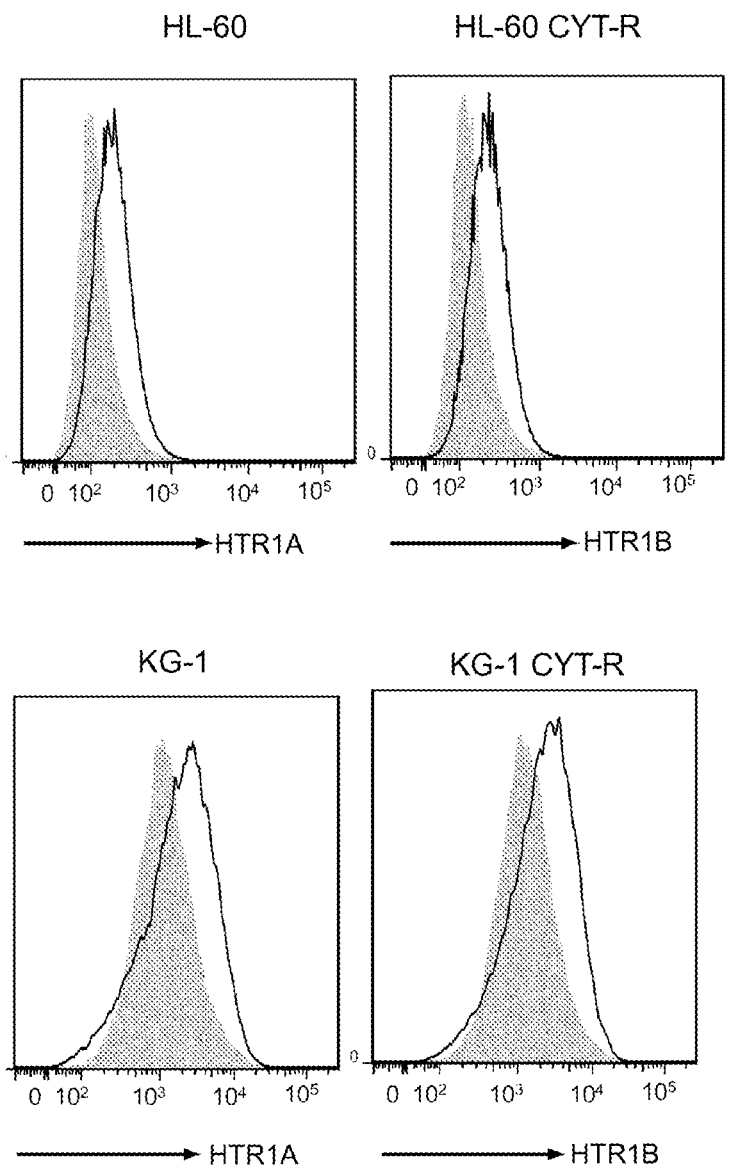
Figure 6C:
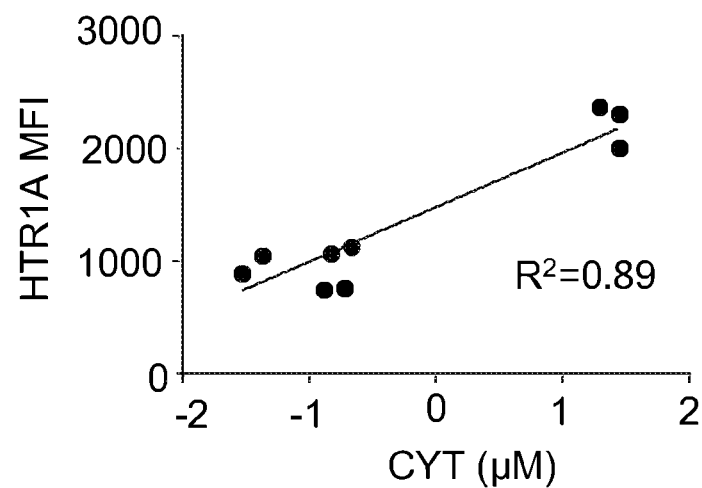
Figure 6C:
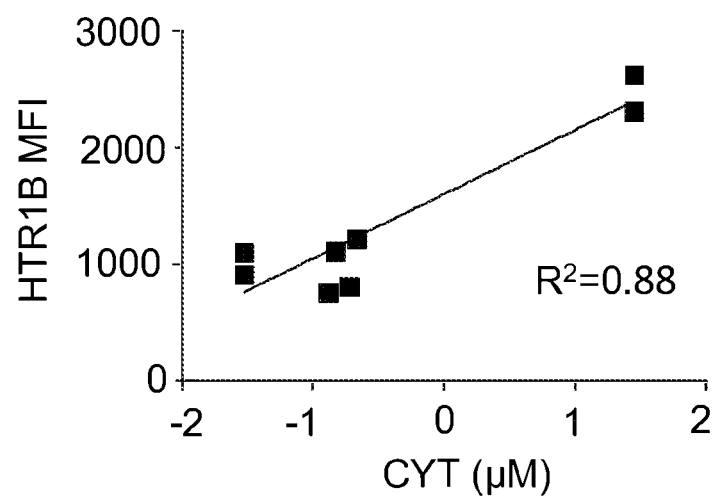

Next, the expression of HTR1A and HTR1B on the surface by flow cytometry was measured. Ara-C-resistant AML cells expressed higher levels of HTR1A and HTR1B compared to the parental cell line (FIGS. 6A and 6B). In fact, an inverse correlation between HTR1A and HTR1B expression level and sensitivity to Ara-C was found (FIG. 6C); thus, AML cell lines with the highest receptor expression showed the highest resistance to Ara-C.

Example 7-HTR1 Antagonists Decrease Sp1 Expression

Figure 7:
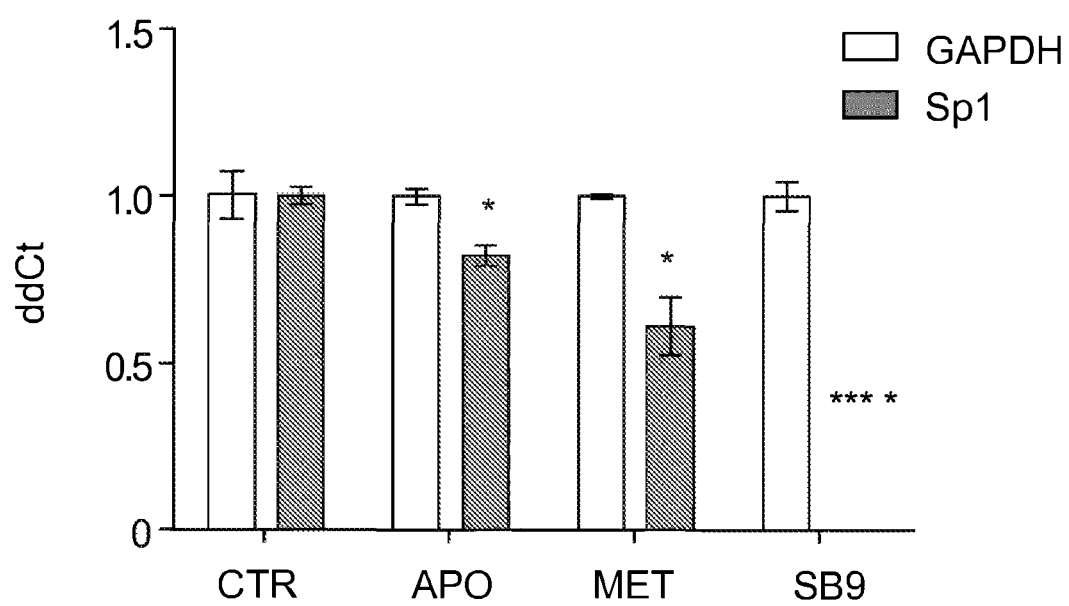
FIG. 7. Treatment with HTR1 antagonists decreased Sp1 gene expression. HL-60 AML cells were treated with 10 μM apomorphine (APO), 10 μM methiothepin (MET) or 5 μM SB224289 (SB9) for 72 h. Total RNA was isolated and cDNA was obtained afterwards. Semi-quantitative PCR was performed to detect gene expression. Sp1 gene expression is represented as $2^{(-\Delta\Delta Ct)}$ using GAPDH as the endogenous control. Bars represent the mean value of triplicates. Error bars correspond to SEM. * p<0.05; **** p<0.0001. ddCt: $2^{(-\Delta\Delta Ct)}$.

At a gene expression level, the expression of Sp1 mRNA was studied. Sp1 has been implicated with chemotherapeutic resistance (Zhang et al. Mol Cancer 2015; 14:56). HL-60 AML cells were treated for 72 h with 10 UM apomorphine, 10 UM methiothepin and 5 UM SB224289. Total RNA as isolated and mRNA was retrotranscribed to cDNA. Semi-quantitative PCR was performed with specific TaqMan oligo pairs. As shown in FIG. 7, HTR1 antagonist treatment produced the downregulation of Sp1 gene expression.

Example 8—Synergistic Effect of Cladribine and HTR1 Antagonists

Figure 8A:
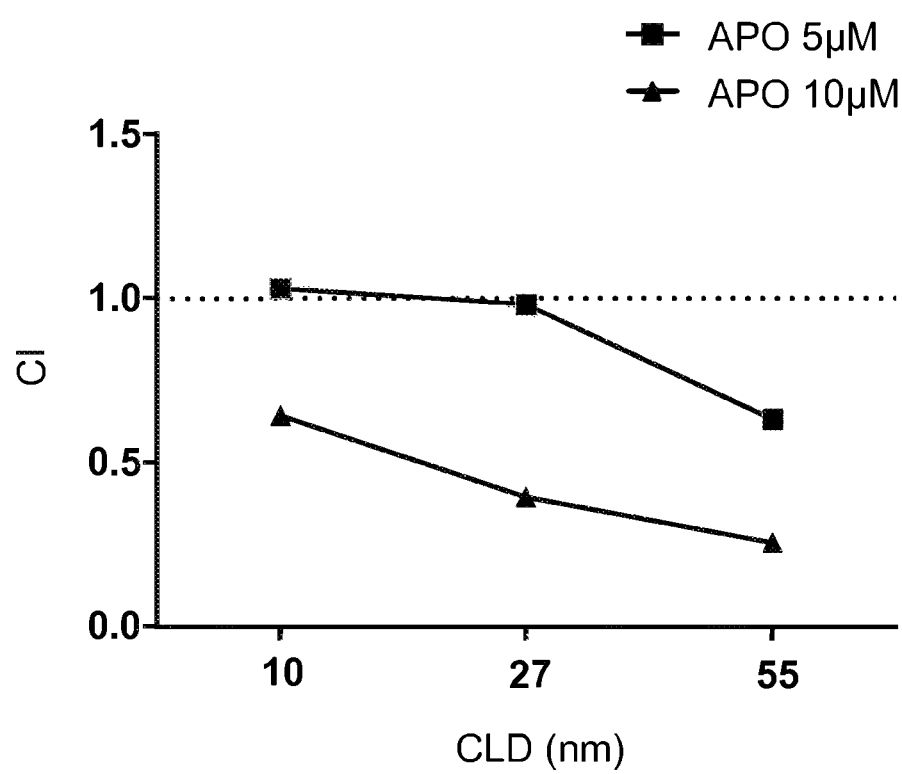
FIGS. 8A and 8B. Cladribine displayed a synergistic anti-neoplastic effect combined with HTR1 antagonists on AML cells. MonoMac-1 cells were cultured for 72 h in a complete RPMI medium in the presence of 5, 10 µM apomorphine (APO) or methiothepin (MET), and 10, 27, 55 nM cladribine (CLD).
Figure 8B:
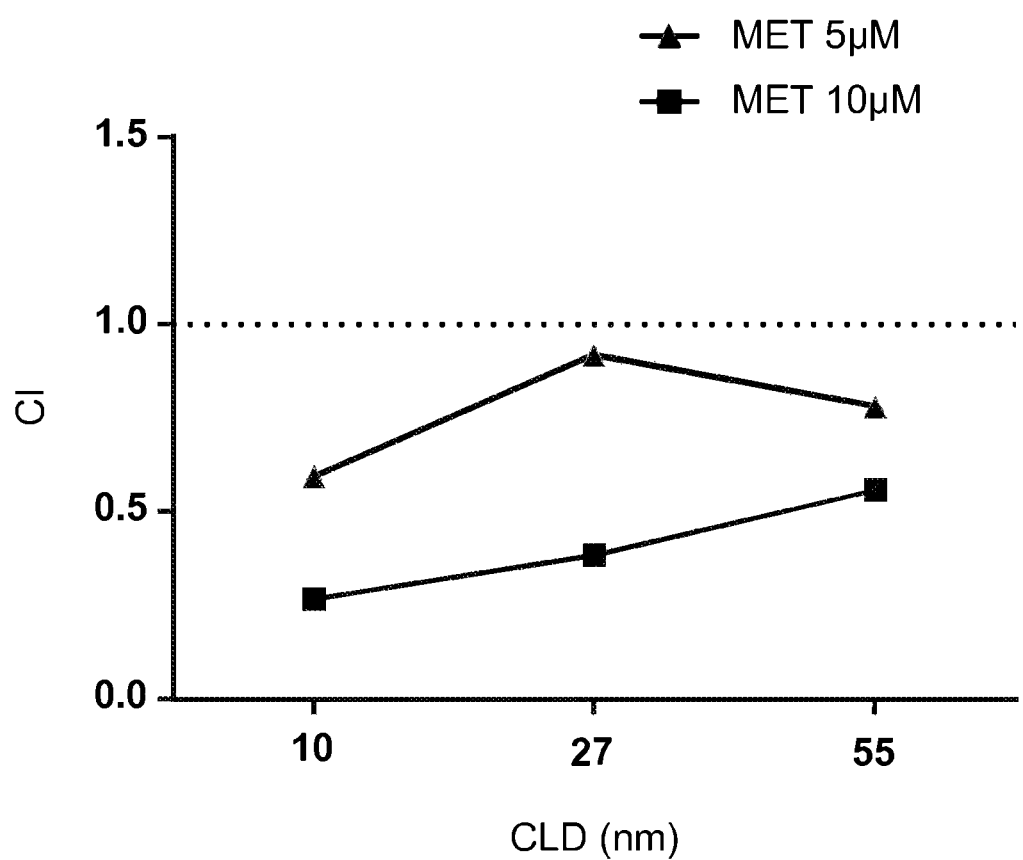

Similar to the examples 1-3, cladribine was also interrogated for its potential cytotoxic interaction with HTR1 antagonists. Cladribine is a cytostatic drug indicated for myeloid neoplasias. AML cell line (MonoMac-1) was treated with different concentrations of HTR1 antagonists (apomorphine and methiothepin) in the presence of a range of concentrations of cladribine. 72 h after treatment, cell viability was measured by flow cytometry (live cells according to the correct FSC-SSC profile, 7-AAD negativity and Hoechst 33342 positivity, and volumetrically counted). As shown in FIGS. 8A and 8B, both HTR1 antagonists displayed a synergically anti-leukemic effect from a molar relationship of 100:1 to 1000:1 (HTR1:cladribine).

Example 9—Synergistic Effect of Fludarabine and HTR1 Antagonists

Figure 9A:
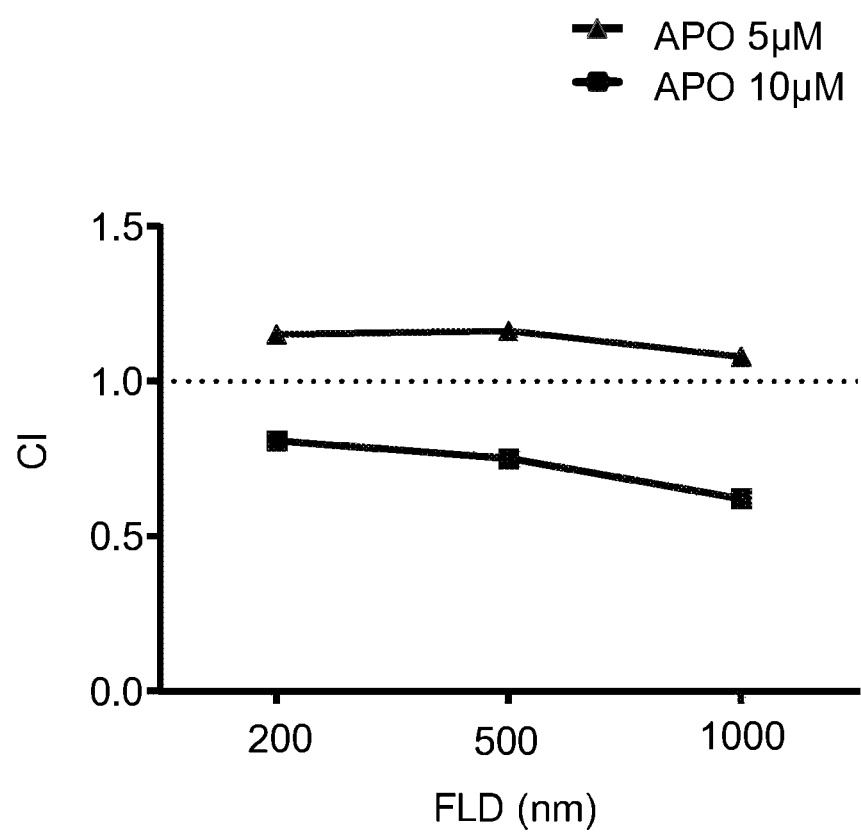
FIGS. 9A and 9B. Fludarabine displayed a synergistic anti-neoplastic effect combined with HTR1 antagonists on AML cells. MonoMac-1 cells were cultured for 72 h in a complete RPMI medium in the presence of 5, 10 µM apomorphine (APO) or methiothepin (MET), and 200, 500, 1000 nM fludarabine (FLD).
Figure 9B:
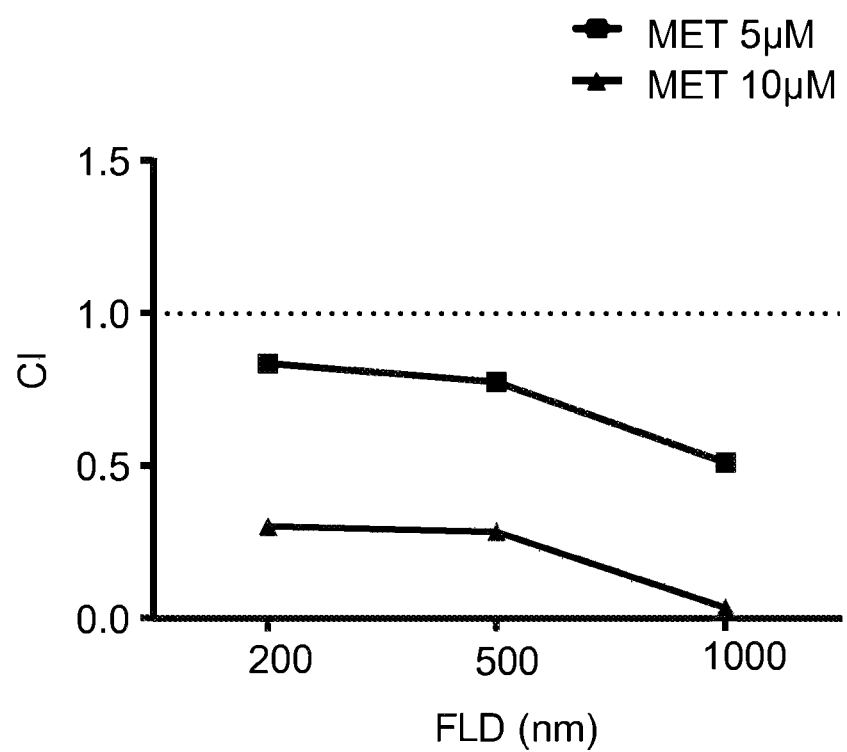

The potential cytotoxic interaction of fludarabine with HTR1 antagonists was also examined on the same experimental conditions of the example 8. AML cell line (MonoMac-1) was treated with different concentrations of HTR1 antagonists (apomorphine and methiothepin) in the presence of a range of concentrations of fludarabine. 72 h after treatment, cell viability was measured by flow cytometry (live cells according to the correct FSC-SSC profile, 7-AAD negativity and Hoechst 33342 positivity, and volumetrically counted). As shown in FIGS. 9A and 9B, both HTR1 antagonists displayed a synergically antileukemic effect from a molar relationship of 5:1 to 50:1 (HTR1: fludarabine).

Example 10—Synergistic Effect of Methotrexate and HTR1 Antagonist

Figure 10:
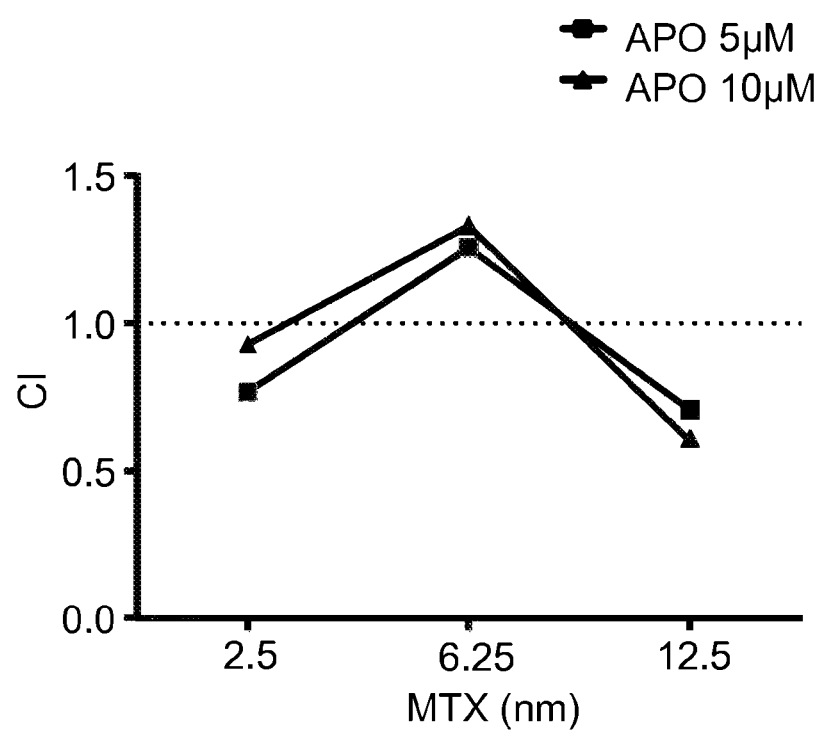
FIG. 10. Methotrexate displayed a synergistic anti-neoplastic effect combined with apomorphine on AML cells. MonoMac-1 cells were cultured for 72 h in a complete RPMI medium in the presence of 5, 10 µM apomorphine (APO), and 2.5, 6.25, 12.5 nM methotrexate (MTX). CI value of MTX and APO combination.

Finally, the interaction of the antineoplastic drug methotrexate with HTR1 antagonist was studied. AML cell line (MonoMac-1) was treated with different concentrations of HTR1 antagonist (apomorphine) in the presence of a range of concentrations of methotrexate. 72 h after treatment, cell viability was measured by flow cytometry (live cells according to the correct FSC-SSC profile, 7-AAD negativity and Hoechst 33342 positivity, and volumetrically counted). As shown in FIG. 10, HTR1 antagonist displayed a synergically anti-leukemic effect from a molar relationship of 400:1 to 4000:1 (HTR1:methotrexate), in low and high concentrations.

The invention claimed is:

1. A synergistic combination for the treatment of a hematological malignancy comprising
   (a) an ATC/DDD L01B antimetabolite; and
   (b) a type 1A or type 1B HTR serotonin receptor (HTR1A or HTR1B) small molecule antagonist, at a molar ratio of HTR1A or HTR1B small molecule antagonist to ATC/DDD L01B antimetabolite between
      (i) 500:1 and 2:1 when the ATC/DDD L01B antimetabolite is a pyrimidine analogue;
      (ii) 1000:1 and 5:1 when the ATC/DDD L01B antimetabolite is a purine analogue; or
      (iii) 4000:1 to 400:1 when the ATC/DDD L01B antimetabolite is a folic acid analogue;
   wherein the synergistic combination comprising the ATC/DDD L01B antimetabolite and the HTR1A or HTR1B small molecule antagonist is capable of synergistically killing hematological malignancy cells expressing HTR1A or HTR1B.

2. The synergistic combination of claim 1, wherein the ATC/DDD L01B antimetabolite is a folic acid analogue selected from the group consisting of methotrexate, raltitrexed, pemetrexed, and pralatrexate.

3. The synergistic combination of claim 1, wherein the ATC/DDD L01B antimetabolite is a pyrimidine analogue selected from the group consisting of cytarabine, fluorouracil, tegafur, carmofur, gemcitabine, capecitabine, azacitidine, decitabine, and trifluridine.

4. The synergistic combination of claim 1, wherein the ATC/DDD L01B antimetabolite is a purine analogue selected from the group consisting of mercaptopurine, tioguanine, cladribine, fludarabine, clofarabine, and nelarabine.

5. A pharmaceutical composition comprising a synergistic combination of claim 1 and a pharmaceutically acceptable excipient.

6. A method for treating a hematological malignancy comprising administering a synergistic combination of claim 1 to a subject in need thereof.

7. The method of claim 6, wherein the hematological malignancy is a myeloid neoplasm.

8. The method of claim 7, wherein the myeloid neoplasm is acute myeloid leukemia.

9. The method of claim 6, wherein the hematological malignancy is selected from the group consisting of a myelodysplastic syndrome and a myeloproliferative syndrome.

10. The method of claim 6, wherein the ATC/DDD L01B antimetabolite and the HTR1A or HTR1B small-molecule drug antagonist are administered independently or at the same time.

11. The method of claim 6, wherein the HTR1A or HTR1B small-molecule drug antagonist is in an amount between 0.1 mg/m$^2$ and 100 mg/m$^2$.

12. A dosage form comprising a synergistic combination of
   (a) an ATC/DDD L01B antimetabolite; and
   (b) a type 1A or type 1B HTR serotonin receptor (HTR1A or HTR1B) small molecule antagonist, at a molar ratio of HTR1A or HTR1B small molecule antagonist to ATC/DDD L01B antimetabolite between
      (i) 500:1 and 2:1 when the ATC/DDD L01B antimetabolite is a pyrimidine analogue;
      (ii) 1000:1 and 5:1 when the ATC/DDD L01B antimetabolite is a purine analogue; or
      (iii) 4000:1 to 400:1 when the ATC/DDD L01B antimetabolite is a folic acid analogue;
   wherein the synergistic combination comprising the ATC/DDD L01B antimetabolite and the HTR1A or HTR1B small molecule antagonist is capable of synergistically killing hematological malignancy cells expressing HTR1A or HTR1B.

13. The dosage form of claim 12, wherein the HTR1A or HTR1B small-molecule drug antagonist is in an amount between 0.1 mg/m2 and 100 mg/m2.

14. The dosage form of claim 12, wherein the dosage form is suitable for intravenous administration.

15. The dosage form of claim 14, wherein the intravenous administration is by infusion or by bolus injection.

* * * * *